United States Patent [19]

Kopf

[11] Patent Number: 4,882,050
[45] Date of Patent: Nov. 21, 1989

[54] FILTER PLATE, FILTER PLATE ELEMENT, AND FILTER COMPRISING SAME

[76] Inventor: Henry B. Kopf, 108 Coatbridge Cir., Cary, N.C. 27551

[21] Appl. No.: 235,046

[22] Filed: Aug. 22, 1988

Related U.S. Application Data

[63] Continuation-in-part of Ser. No. 104,177, Oct. 2, 1987.

[51] Int. Cl.[4] .................... B01D 25/12; B01D 13/00
[52] U.S. Cl. .................... 210/231; 210/321.75; 210/321.84; 210/456
[58] Field of Search .................... 210/321.75, 321.84, 210/445, 456, 488, 227, 228, 231

[56] References Cited

U.S. PATENT DOCUMENTS

| | | | |
|---|---|---|---|
| 3,585,131 | 6/1971 | Esmond | 210/321.77 |
| 3,966,612 | 6/1976 | Johansson | 210/521.75 |
| 4,229,304 | 10/1980 | Fismer | 210/231 |
| 4,310,416 | 1/1982 | Tanaka | 210/321.75 |
| 4,411,784 | 10/1983 | Esmond | 210/321.75 |
| 4,430,218 | 2/1984 | Perl | 210/321.75 |
| 4,540,492 | 9/1985 | Kessler | 210/321.75 |
| 4,543,187 | 9/1985 | Steppacher | 210/231 |
| 4,735,718 | 4/1988 | Peters | 210/321.84 |
| 4,750,983 | 6/1988 | Foster | 210/321.75 |
| 4,769,140 | 9/1988 | Van Dijk | 210/321.75 |

FOREIGN PATENT DOCUMENTS 1392030  4/1975  United Kingdom ................ 210/231

OTHER PUBLICATIONS

Millipore Corporation Sales Literature, 8/88—SD 200 Copywrite 1988 Millipore Corporation—Prostak Cross Flow.
Millipore Corporation Sales Literature—Labratory Ultrafiltration Products for Improved Biological Recovery—10/88— ©1988 Millipore Corp.

Primary Examiner—David L. Lacey
Assistant Examiner—Thomas M. Lithgow
Attorney, Agent, or Firm—Steven J. Hultquist

[57] ABSTRACT

A filter plate which is longitudinally partitioned between its inlet and outlet ends, and features liquid feed and collection troughs at the respective ends. Such plates may be associated in opposed, relatively inverted pairs to form enclosed flow channels characterized by fluid flow rates which are substantially uniform across the full transverse extent of the flow path and which facilitate the utilization of the full areal extent of the filter media employed therewith. Also described is a unitary filter element which may be usefully employed in the filter. The filter of the invention may be highly efficiently employed for dewatering of aqueous biomass suspensions, desalting of proteins, removal of secreted metabolites from cellular suspensions, and the like.

6 Claims, 16 Drawing Sheets

FILTER PLATE, FILTER PLATE ELEMENT, AND FILTER COMPRISING SAME

CROSS-REFERENCE TO RELATED APPLICATION

This is a continuation-in-part of U.S. application Ser. No. 07/104,177 filed Oct. 2, 1987 in the name of Henry B. Kopf.

BACKGROUND OF THE INVENTION

1. Field of The Invention

This invention relates generally to cross-flow filters comprising a multiplicity of stacked filter plates, of a type wherein filter elements are disposed between adjacently paired stacked plates.

2. Description of the Related Art

Stacked plate cross-flow filters are utilized in a variety of solids-liquid separation operations, including the dewatering of solids-liquid suspensions such as aqueous biomass suspensions, the desalting of proteins, and the removal of secreted metabolites from cellular cultures. In such systems, the stacked plates making up the cross-flow filter are typically mounted in a unitary frame structure whereby the respective plates are retained in alignment, in a so-called "plate and frame" construction. A unitary liquid feed conduit provided with openings at spaced intervals along its length and extending through the stacked plates is typically employed as a feed means from which influent solids-containing liquid is introduced into the flow channels defined between adjacent plates in the stacked plate assembly. The flow channels in the plate and frame filter contain filter elements, such as disposable filter paper sheets, with which the solids-containing liquid is contacted and through which solids-depleted liquid passes. A unitary liquid withdrawal conduit featuring openings at spaced intervals along its length extends through the stacked plates in liquid flow communication with the respective flow channels of the stacked plate assembly and conveys solids-depleted liquid out of the filter system.

As filtration proceeds, the filtered solids build up in the flow channels of the filter, on the "feed liquid sides", i.e., active filtration surfaces, of the filter sheets. The filter is then periodically backwashed, or alternatively, it may be fully shut down after a predetermined level of solids has accumulated in the flow channels on the filtration surfaces of the filter sheet elements, following which the system is drained of liquid, and the filter sheets replaced as necessary.

In one type of presently marketed stacked filter system, commercially available from Millipore Corporation (Bedford, Massachusetts) as the Prostak ® cross-flow filter, the adjacent filter plates define a flow channel. Solids-containing influent liquid is fed at one side of the plate from a central location into a transversely extending feed distribution conduit, which is provided with openings at spaced apart intervals along the length of the conduit for egress of the solids-containing liquid. At the opposite side of the adjacent plates, the flow channel is similarly constructed with a liquid collection conduit having openings along its length to collect the solids-depleted liquid and discharge same from a central outlet communicating with the collection conduit.

A major problem which has been encountered in cross-flow filters of the above-described type is that the liquid flow distribution, as for example reflected by the volumetric liquid flow rate or liquid superficial velocity, is highly non-uniform in the transverse direction of the flow channel. Such maldistribution of the solids-containing liquid is a result of the fact that the influent liquid is introduced into the feed distribution conduit at a central location. Due to the pressure drop in the transverse direction, from the medial inlet port out to the extremities of the feed distribution conduit, the local longitudinal flow (cross-flow) of liquid from the inlet side to the outlet side of the stacked plates, at progressively farther transverse distances from the central liquid inlet port, is progressively reduced to an extent which is commensurate with the pressure drop experienced as the liquid is directed transversely to the outer extremities of the distribution conduit. As a result, there is preferential channeling of the liquid at the central part of the flow channel from the inlet side to the outlet side thereof, and concomitant under-utilization of the peripheral areas of the filter. When the solids in the central portion have been built up to a point requiring backwashing or draining of the filter, the peripheral areas of the filter still have available capacity to separate solids from the feed liquid.

Such transverse maldistribution of the feed liquid in cross-flow filters of the aforementioned type could conceivably be overcome by the provision of header manifolds to introduce feed liquid into the filtration channels at multiple introduction points along the sides of the stacked filter plates, with a corresponding outlet header manifold arrangement at the opposite side of the stacked plates. Unfortunately, however, such provision would significantly increase the overall system pressure drop as well as the complexity of the filter system, since it could be necessary to positively seal the multiplicity of feed liquid branch lines passing from the manifold into the filter.

Another type of stacked plate cross-flow filter which has been commercialized employs a transversely extending liquid distribution conduit with spaced apart openings therein to introduce solids-containing liquid into the flow channel between adjacent stacked plates, but instead of a central inlet port to flow the solids-containing liquid to such conduit, the liquid is axially fed into the conduit from a feed line connected to a transverse extremity of the conduit. Filters of such type are available from Millipore Corporation (Bedford, Massachusetts) under the trademark Pellicon ®. This feed arrangement results in a progressive diminution of the liquid pressure at increasing transverse distances from the feed end of the distribution conduit, which in turn results in progressively transversely decreased cross-flow rates of liquid in the flow channel.

In an effort to overcome the aforementioned liquid flow maldistribution characteristics of stacked plate filters, filter plates have been constructed with baffle elements defining discrete flow channels, with the intent of achieving a more uniform distribution of the solids-containing influent liquid across the full areal extent of the filter elements in the flow channels of the filter.

A filter plate commercially available from Toyo Soda Manufacturing Company, Ltd. (Tokyo, Japan) features a structure in which solids-containing influent liquid is introduced to the flow channel at a central inlet port at one side of the plate. A wall is disposed in front of the liquid inlet, extending upwardly from the floor of the flow channel and transversely toward the extremities of the flow channel, to divide the influent stream into two outwardly directed streams. Downstream from such stream-splitting wall is a longitudinally extending divider partition, the stream-splitting wall and the divider partition together forming a "T" construction when viewed in plan view. Longitudinally spaced from and parallel to the stream-splitting wall are a series of baffle partitions on either side of the divider partition. The baffles extend transversely part way across the flow channel on either side of the divider partition, so that there is formed a serpentine flow path for each of the split streams, on the respective sides of the partition. A unitary liquid outlet port is provided at the opposite side of the stacked plates from the inlet port, whereby the respective serpentine flows are finally joined and discharged from the flow channels of the filter.

Although the dual serpentine flow path arrangement described above provides a somewhat better distribution of liquid flow across the areal extent of the filter paper element, the sharp turns in the flow path at the extremities of the baffles create edge and entrance effects in the flow streams which produce substantial dead space and bypassing therein. As a result of such anomalous flow phenomena, the filtration efficiency of the baffled serpentine flow arrangement is significantly reduced.

My prior copending U.S. application Ser. No. 07/104,177 filed Oct. 2, 1987 describes a filter plate characterized by substantially uniform transverse distribution of liquid from a unitary liquid feed port, and highly uniform liquid cross-flow across the full transverse extent of the flow channel formed when plates of such type are stacked to form a cross-flow filter.

The filter plate of this copending application has a generally planar and rectangular shape with a substantially flat bottom surface. A top surface of the plate is provided with an upwardly extending wall circumscribingly bounding a flow channel of generally rectangular shape. A liquid inlet port is disposed at a medial part of a first side of the flow channel, with the liquid outlet port at a medial part of a second side of the flow channel opposite the first side thereof. The liquid inlet port is joined in liquid flow communication with a liquid feed trough extending transversely across the first side of the flow channel, and the liquid outlet port is joined in liquid flow communication with a liquid collection trough extending transversely across the second side of the flow channel.

In this construction, a plurality of spaced-apart partitions extend upwardly from the floor of the flow channel between the liquid feed trough and the liquid collection trough. These partitions are of lesser height than the walls circumscribing the flow channel and are substantially parallel to one another, to define a series of sub-channels extending longitudinally between the liquid feed trough and the liquid collection trough. Both the liquid feed trough and the liquid collection trough are of progressively increasing depth from their respective medial portions to their marginal extremeties.

Plates of this prior copending application may be utilized in stacked pairs to form enclosed flow channels within which filtration may take place in a highly efficient manner. Specifically, a first plate of the type broadly described above is paired with a structurally identical second plate positioned in inverted relationship to the first plate, such that the respective circumscribingly bounding walls of the first and second plates are in abutting sealing contact with one another. In this stacked arrangement, a filter element support of generally rectangular shape approximating the dimensions of the flow channel is interposed between the adjacent plates, with filter sheet elements between the support and each of the respective paired filter plates.

It is an object of the present invention to provide a filter plate of an improved type, which is simple and efficient in construction and operation.

It is another object of the invention to provide a filter comprising stacked filter plates of such type.

Other objects and advantages of the invention will be more fully apparent from the ensuing disclosure and appended claims.

SUMMARY OF THE INVENTION

In a broad aspect, the present invention relates to a filter plate suitable for use with filter elements to form a stacked plate filter. In the stacked plate filter, pairs of such filter plates are mated with filter elements therebetween, to form flow channels wherein solids-containing liquid may be contacted with the filter sheet elements for filtration thereof to produce solids-reduced liquid, and permeate.

The filter plate of the invention has a generally planar shape with a substantially flat bottom surface. A top surface of the plate is provided with a first upwardly extending wall circumscribingly bounding a flow channel of generally rectangular shape.

The flow channel also is circumscribingly bounded by a 15 second upwardly extending wall interior to and of lesser height than the first circumscribingly bounding wall, the second wall being in spaced-relation to the outer wall along diagonally opposed L-shaped peripheral sections of the flow channel, each such L-shaped peripheral section comprising a leg extending transversely across the flow channel for a major portion of the length thereof, and a leg extending longitudinally for a portion of the longitudinal dimension of the flow channel and communicating at its extremity with an opening extending through the plate, with the portions of the periphery of the flow channel not comprising such L-shaped sections comprising ridge elements extending between the first and second circumscribingly bounding walls.

A liquid inlet port is disposed at a first side of the flow channel, with a liquid outlet port at a second side of the flow channel opposite the first side thereof.

The liquid inlet port is joined in liquid flow communication with a liquid feed trough interior to the second bounding wall and extending transversely across the first side of the flow channel. The liquid outlet port is joined in liquid flow communication with a liquid collection trough interior to the second bounding wall and extending transversely across the second side of the flow channel.

A plurality of spaced-apart partitions extend upwardly from the floor of the flow channel between the liquid feed trough and the liquid collection trough. Such partitions are substantially parallel to one another to define a series of sub-channels extending longitudinally between the liquid feed trough and the liquid collection trough. These partitions preferably are of lesser height than the first (outer) wall circumscribing the flow channel and of substantially the same height as the second (inner) wall circumscribing the flow channel.

Plates of the foregoing type may be utilized in stacked pairs to form enclosed flow channels within which filtration may take place in a highly efficient manner. Specifically, a first plate of the type broadly described above may be paired with a corresponding second plate positioned in inverted relationship to the first plate, such that the respective first circumscribingly bounding walls of the first and second plates are in abutting sealing contact with one another. In such stacked arrangement, a filter element of generally rectangular shape approximating the dimensions of the flow channel is interposed between the adjacent plates, suitably with its peripheral edges reposed on the second bounding wall. Such filter element is provided with an interior flow structure, whereby permeate entering the interior of the element is conveyed to the edge portions of the element for discharge into the aforementioned L-shaped peripheral sections of the flow channel between the respective first and second bounding walls. In an illustrative aspect, the filter element may comprise a foraminous support of generally rectangular shape approximating the dimensions of the flow channel, interposed between the adjacent plates, with filter sheet elements between the foraminous support and each of the respective filter plates.

In the operation of such a stacked filter plate assembly, liquid introduced via the liquid inlet port enters the liquid feed trough and is laterally distributed from the associated portion of the feed trough to outer extremities thereof. The liquid flow is directed into the sub-channels to yield a longitudinal liquid cross-flow which is highly uniform over the full transverse extent of the flow channel, so that the full areal extent of the filter element is highly effectively utilized. As a result, the solids filtration capacity of the stacked plate assembly is substantially increased and the assembly is capable of significantly extended operation prior to regeneration of the filter, as compared to various prior art cross-flow plate and frame filters illustratively described in the preceding section hereof.

In another aspect, the invention relates to a filter element which may be usefully employed with filter plates of the type described above, in stacked plate filter assemblies. The filter element comprises a support which includes a circumscribing frame with an array of spaced-apart and substantially parallelly aligned ribs extending between and joined at their opposite ends to the frame, so that the ribs and frame form a series of corresponding substantially parallel filtrate (permeate) flow channels. The circumscribing frame includes diagonally opposed marginal flanges, i.e., projections extending from respective diagonally opposed corners of the frame longitudinally along the margins of the frame part way toward the respective opposite ends of the frame.

Openings are provided in the frame, preferably at opposite end edge surfaces of the frame, in liquid flow communication with the filtrate flow channels, for egress of filtrate from the filtrate flow channels through the frame openings.

In the filter element, a first filter sheet is secured along its margins to a first face of the frame, and a second filter sheet is correspondingly secured along its margins to a second face of the frame. The first and second filter sheets together with the frame define an enclosed interior volume comprising the filtrate flow channels separated by the ribs.

In this manner, filtrate entering the interior of the filter element through the first and second filter sheets is able to flow in the filtrate flow channels and be discharged from the filter element through the frame openings which are in liquid flow communication with the filtrate flow channels.

In another aspect, the present invention relates to a filter plate of generally planar shape with a substantially flat bottom surface, and a top surface with an upwardly extending wall circumscribingly bounding a flow channel, accommodating insertion of a filter element into the flow channel, with the plate being abuttingly and sealing matable with a corresponding plate positioned in inverted relationship with respect thereto, such that the flow channel enclosingly contains the filter element in the flow channel. The flow channel bounding wall in this aspect a keying structure associated therewith for cooperative mating with a complementarily configured structure on a said filter element. As used herein, the term "keying structure" includes a structural element which is lockingly matable with a complementarily configured element. For example, the filter plate may be feature a tab or ridge element extending from the bounding wall toward the interior of the flow channel, with which a filter element comprising a complementarily configured notch may be cooperatively mated to fixedly position the filter element in the flow channel defined by the bounding wall.

In yet another aspect, the present invention relates to a filter plate having a generally planar shape with circumferentially spaced-apart openings about the periphery thereof for mating with rod elements to form a stacked plate filter comprising a multiplicity of such plates, wherein the openings are of at least two different shapes or sizes, whereby the plate may be mated with rods comprising corresponding cross-sectional shapes, so that the filter plate is only matable with said rods in a selected positional orientation.

Still another aspect of the present invention relates to a filter plate having a generally planar shape with a substantially flat bottom surface, and a top surface having an upwardly extending wall circumscribingly bounding a flow channel of generally rectangular shape, with a liquid inlet port at a first side of the flow channel and a liquid outlet port at a second side of the flow channel opposite the first side thereof, the liquid inlet port being joined in liquid flow communication with a liquid feed trough extending transversely across the first side of the flow channel, and the liquid outlet port being joined in liquid flow communication with the liquid collection trough extending transversely across the second side of the flow channel. A plurality of spaced-apart partitions extend upwardly from the floor of the flow channel between the liquid feed trough and the liquid collection trough. The partitions are of substantially the same height as the wall circumscribing the flow channel and are substantially parallel to one another to define a series of sub-channels extending longitudinally between the feed trough and the liquid collection trough. The liquid inlet port has an open area, designated $A_o$, and the sub-channels each have an open area, designated $A_i$, measured in a plane perpendicular to the longitudinal axis of the sub-channel, of a height equal to the height of the partitions and a width equal to the transverse distance between adjacent partitions bounding said sub-channel, wherein $A_o$ is from about 0.8 to about 1.3 the total sub-channel open area $A_s$, wherein and n is the number of sub-channels.

Other aspects and features of the invention will be more fully apparent from the ensuing disclosure and appended claims.

DETAILED DESCRIPTION OF THE INVENTION, AND PREFERRED EMBODIMENTS THEREOF

The filter plate of the present invention is adapted to be employed in multiple pairs to form a stacked plate filter assembly wherein adjacent paired plates are oriented invertedly with respect to one another. In this manner, a single structured configuration may be employed for all of the plates in the stacked assembly, if a "central" inlet and outlet arrangement, as described more fully hereinafter, is employed. If a "side" inlet and outlet arrangement is employed, the plates may be of two structured configurations which are mirror images of one another and are mated with one another in sequential pairs to form the stacked filter assembly.

The filter plates and the interposed foraminous support employed therewith may be formed of any suitable materials of construction, including polypropylene, polyethylene, polysulfone, polyimide, polyvinyl chloride, regenerated cellulose, polycarbonate, cellulose acetate, cellulose triacetate, cellulose nitrate, mixed esters of cellulose, etc.; ceramics e.g., oxides of silicon, zirconium, and/or aluminum; metals such as stainless steel; polymeric fluorocarbons such as polytetrafluoroethylene; and compatible alloys, mixtures, and composites of such materials.

Preferably, the plates and interposed filter element support are made of materials which are adapted to accommodate high temperatures, so that the interior surfaces of the filter may be steam sterilized and/or chemically sanitized for regeneration and reuse. Steam sterilization may typically be carried out at temperatures on the order of from about 121° C. to about 130° C., and a pressure of 15-30 psi, with the sterilization exposure time typically being from about 15 minutes to about 2 hours, or even longer.

Figure 1:
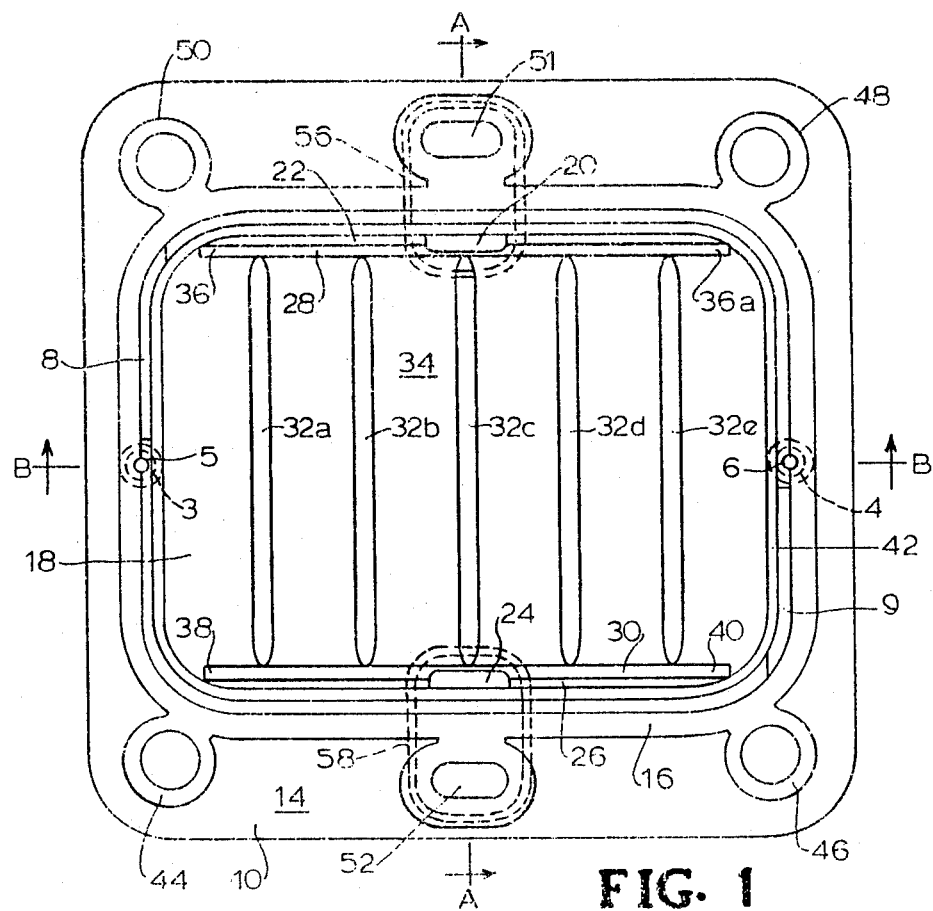
FIG. 1 is a top plan view of a filter plate according to the present invention.
Figure 2:
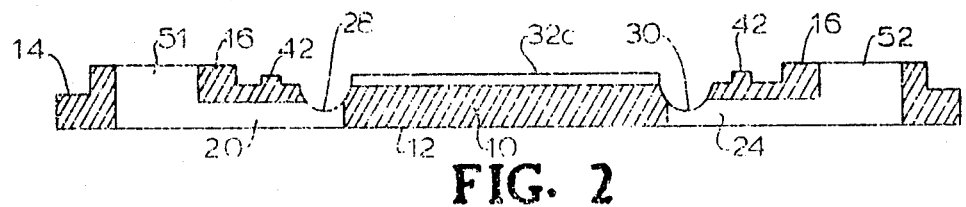
FIG. 2 is a sectional elevation view of the filter plate of FIG. 1, taken along line A—A thereof.
Figure 3:
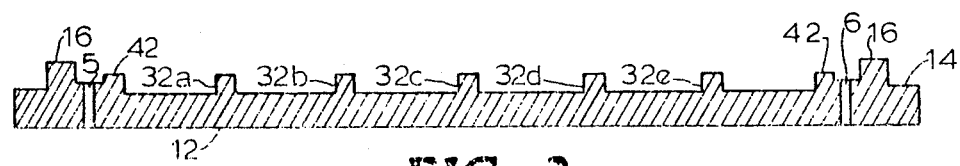
FIG. 3 is a sectional elevation view of the filter plate shown in FIG. 1, taken along line B—B thereof.

FIG. 1 shows an illustrative filter plate according to the present invention, in plan view. FIG. 2 shows a sectional elevation view of the FIG. 1 plate, taken along line A—A thereof, and FIG. 3 is a sectional elevation view of the FIG. 1 plate, taken along line B—B thereof.

Referring to these drawings, the plate member 10 is generally planar and may be rectangular in shape, having a generally square shape in the specific embodiment shown in FIG. 1. The plate has a substantially flat bottom surface 12 (see FIGS. 2 and 3), and a top surface 14 which is substantially flat in the peripheral portions of the plate. The top surface 14 has an upwardly extending wall 16 circumscribingly bounding a flow channel 18 of generally rectangular shape within the bounding wall.

A liquid inlet port 20 is provided at a medial part of a first side 22 of the flow channel. A liquid outlet port 24 is correspondingly provided at a medial part of a second side 26 of the flow channel opposite the first side thereof. This is the "center" inlet and outlet arrangement referred to hereinabove.

The liquid inlet port 20 is joined in liquid flow communication with a liquid feed trough 28 extending transversely across the first side of the flow channel. Correspondingly, the liquid outlet port 24 is joined in liquid flow communication with a liquid collection trough 30 extending transversely across the second side of the flow channel.

A plurality of spaced apart partitions 32a, 32b, 32c, 32d, and 32e, extend upwardly from the floor 34 of the flow channel between the liquid feed trough 28 and the liquid collection trough 30. The partitions 32a–32e are of lesser height than the wall 16 circumscribing the flow channel and are substantially parallel to each other, to define a series of sub-channels extending longitudinally between the liquid feed trough and the liquid collection trough.

The liquid feed trough 28 preferably is of uniform depth across its full lateral extent, for ease of manufacture, but may if desirable have a laterally varying depth, e.g., the trough may be of progressively decreasing depth from its medial portion, in communication with the liquid inlet port, to its marginal extremities 36 and 36a. The liquid collection trough 30 is of corresponding configuration to the liquid trough 28. As used in this context, the term "depth" refers to the maximum vertical dimension of the feed or collection trough as measured from the bottom of the trough to the plane of the floor 34 of the flow channel 18.

Optionally, the plate may feature, as shown in FIG. 1, an interior circumscribing wall 42 of lesser height than the circumscribing main wall 16, to provide a bearing structure for retention of the support shown in FIGS. 4-5 and described more fully hereinafter.

The outer circumscribing wall 16 may as shown be formed with integral cylindrical flanges 44, 46, 48, and 50, each of which circumscribes a circular opening in the periphery of the plate to accommodate the positioning of the plate on spaced-apart rods, as hereinafter shown with reference to FIG. 6 hereof.

At the medial portions of the first and second sides of the plate, there are provided respective oblong openings 51 and 52 to accommodate the liquid feed and liquid withdrawal conduits which are employed to introduce liquid to and remove liquid from the flow channels defined by adjacently paired stacked plates. Such feed and discharge liquid conduits are more fully shown and described with reference to FIG. 6 herein. The respective liquid feed and discharge conduits are suitably formed with spaced-apart perforations therein which permit egress or ingress of liquid into or out of the flow channel via the above-described respective liquid inlet and outlet ports of the plate. In order to assure positive sealing of the flow channels and adjacently positioned plates relative to the liquid feed and discharge conduits the liquid inlet and outlet ports of the plate are suitably provided with gasket elements 56 and 58 as shown in FIG. 1, at the bottom surface 12 of the plate.

As an example of plate dimensional characteristics for an illustrative embodiment of the invention, a filter plate suitable for filtration of aqueous biomass suspensions may be generally of square shape as shown in FIG. 1 with sides on the order of about 6 inches, and with feed and collection troughs 28 and 30 which are each 2 millimeters deep at their medial portions, continously decreasing to a depth of 1.5 millimeters at their respective extremities (peripheral portions 36 and 36a of feed trough 28, and peripheral portions 38 and 40 of collection trough 30). The transverse dimension (width) of each of the sub-channels defined by the partition walls 32a-e is approximately 2 centimeters.

The details of the plate construction are shown in FIG. 2 with respect to the structural features of the liquid inlet port 20 and liquid outlet port 24. All structural elements and features are numbered correspondingly in FIGS. 2 and 3 with respect to the same system elements of FIG. 1.

As previously described, the filter plate may be provided with a circumbscribing main wall 16 and an interior circumscribing wall 42 of lesser height than the main wall. Between these respective walls is formed a circumscribing channel (see FIGS. 2 and 3), into which suitable openings 5 and 6 may communicate as shown in FIGS. 1 and 3. These respective openings are usefully employed as filtrate (permeate) flow channels to convey or drain the solids-depleted filtered liquid or other permeate from the stacked plate assembly.

Openings 5 and 6 may also be usefully employed as gas flow openings to assist in draining the stacked plate filter upon cessation of normal operation for regeneration. Thus, when the filter is shut down, gas from a suitable supply source (not shown) may be introduced in openings 5 and/or 6 to pressurize the flow channel 18 to a sufficient extent where the same can be drained of accumulated biomass suspension upon the termination of normal liquid flows through the system.

Similarly, these respective openings could be employed for introduction and egress of steam for steam sterilization of the system or for flowing a chemical sterilant through the flow channel 18 prior to initiation or re-initiation of normal filtration operation.

Figure 7:
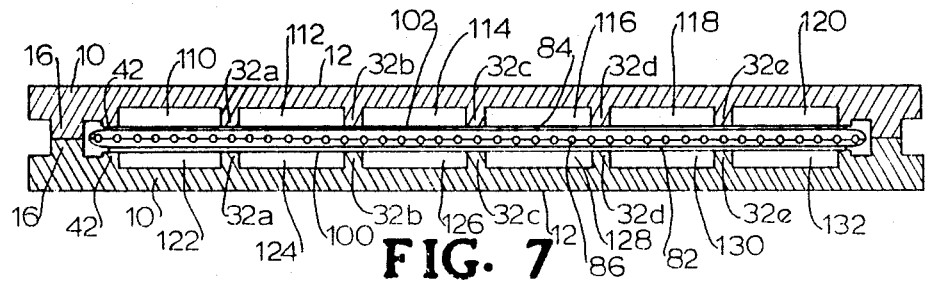
FIG. 7 is a transverse sectional elevation view of a stacked plate filter assembly according to the invention, showing the arrangement of the constituent parts thereof.

Further, because the edges of the foraminous support are disposed in the channel between bounding walls 42 and 16, as shown in FIG. 7, described more fully hereinafter, it is also possible to utilize openings 5 and 6 as respective secondary fluid inlet and discharge passages, for flowing a secondary fluid through the foraminous support for mass transfer contacting of the liquid introduced into the flow channel 18 from inlet port 20 and discharged from the flow channel in outlet port 24. For such purpose, it may be advantageous to symmetrically "block" the channel between bounding walls 42 and 16, at symmetrically opposed regions, as shown in FIG. 1, where channel blocking segment 8 is disposed in the channel along the side thereof containing opening 5, and channel blocking segment 9 is similarly disposed in the channel proximate to opening 6. With such arrangement, fluid entering in opening 5 is diverted downwardly in the channel as shown in the drawing and across the lower portion of the channel as shown until it encounters the channel blocking element 9. Subsequently, when the fluid so introduced is issued from the edges of the foraminous support into the opposite portion of the channel as shown, it flows to outlet opening 6.

Openings 5 and 6 may be appropriately sealed between adjacent plates by provision of suitable gasket means 3 and 4, respectively, at the flat bottom surface 12 of the plate, as shown in dotted line representation in FIG. 1.

Figure 4:
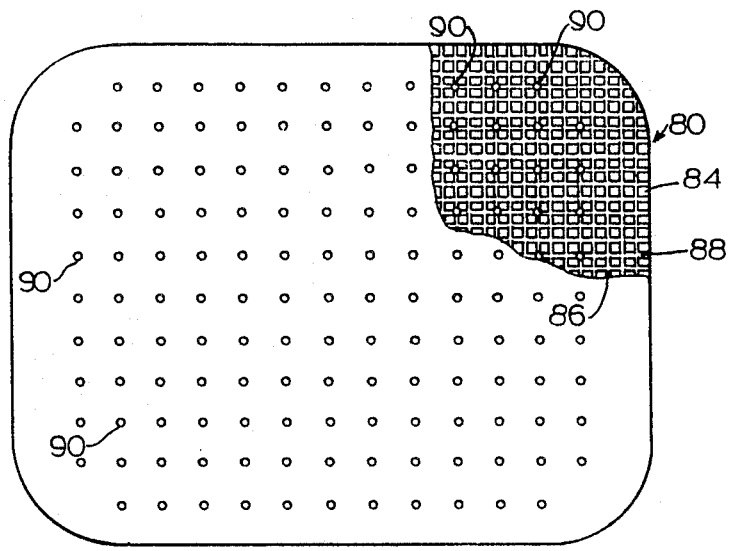
FIG. 4 is a top plan view of a foraminous support suitable for use with paired plates of the type shown in FIGS. 1-3, to form a stacked plate filter assembly.
Figure 5:
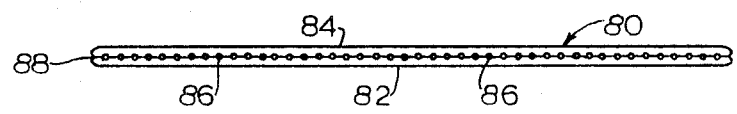
FIG. 5 is an edge elevation view of the foraminous support shown in FIG. 4.

FIGS. 4 and 5 show respective top plan and edge views of an illustrative foraminous support element for the stacked plate filter assembly. Corresponding features of the plate are shown by the same reference numerals in these two drawings.

The foraminous support 80 is simply a support element of generally rectangular shape which is supportively reposable at a first face 82 thereof on the partitions 32a–32e and the circumscribing wall 42 of the plate element, with a first filter sheet, e.g. a filter paper sheet, therebetween.

The foraminous support 80 is likewise supportively reposable at a second face 84 thereof on the partitions and inner bounding wall of a complementary filter plate paired with the filter plate against which the first face 82 of the support is reposed. The second face of the foraminous support likewise has a sheet filter element between its surface and the partitions of the adjacent plate member.

The foraminous support is formed with a plurality of longitudinally extending interior liquid flow channels 86 and a plurality of transversely extending interior liquid flow channels 88, wherein the longitudinal and transverse channels criss-cross one another to establish an extended interconnected network for liquid flow through the interior of the support element. Concurrently connecting the internal liquid flow network with the top and bottom foraminous support surfaces 84 and 82 on which sheets of filter paper or other filtration sheet members are mounted, is an array of surface openings 90. Thus, when a sheet of filter paper is provided for example on the top surface 84 of the foraminous support, the liquid (permeate) component of the solids-liquid suspension passes through the filter paper and openings 90 into the interior liquid flow network comprising channels 86 and 88, for flow through the foraminous support to the edge regions thereof, where the solids-depleted liquid filtrate issues from the support into the channel between bounding walls 16 and 42 and may be removed via openings 5 and 6.

FIG. 7 is a transverse sectional elevation view of a stacked plate filter assembly according to the invention, showing the arrangement of the constituent parts thereof, and numbered correspondingly to FIGS. 1-5 herein. As shown in FIG. 7, the identical complementary upper and lower plates are mated to one another. To insure positive sealing suitable gaskets (not shown) may be interposed (e.g., in opposing grooves) between the abutting top surfaces of the respective opposed bounding walls 16. A lower filter sheet 100 is disposed between the lower surface 82 of the foraminous support, and the partition bearing surface of the lower filter plate. Likewise, an upper filter sheet 102 is interposed between the top surface 84 of the foraminous support and the partition bearing surfaces of the upper filter plate.

By this arrangement, there is formed a series of sub-channels 110, 112, 114, 116, 118, and 120 between the filter sheet 102 and the upper filter plate, while correspondingly a series of sub-channels 122, 124, 126, 128, 130, and 132 are formed between the filter sheet 100 and the lower filter plate, with the sub-channels being longitudinally bounded by the respective partition walls 32a-32e, as shown.

Although the foraminous support has been shown as a structural element of mat-like form, the function of the support is merely to positionally retain the filter sheet on either side thereof and to accommodate the interior flow of solids-depleted liquid toward the filtrate (permeate) collection means associated with the filter plate.

Accordingly, in lieu of the specific foraminous support structure shown, there may be utilized for the support a conventional wire screen element, or a sintered metal plate, or any other construction which will provide the requisite supportive function for the filter sheets and accommodate flow therebetween toward the liquid permeate collection and discharge means. For example, the foraminous support may comprise a sintered metal or ceramic material, e.g., of alumina, zirconia, etc., having an internal network of interconnected voids with an average void passage diameter which may be on the order of from about 0.1 to about 1 micron, depending on the specific filtering operation being conducted, and the dimensional and filtration characteristics of the components of the influent fed to the filter system which is desired to pass through or to remove by the filter. Such support may have a total void space on the order of from about 50 to about 90% by volume, e.g., about 80% voids.

Further, it is to be recognized that such sintered plate may be glazed or otherwise treated on selected portions of its surface, e.g., along one pair of parallel edges of the plate, to render the plate liquid impermeable in such regions. Thus, the sintered plate could be selectively glazed along one pair of parallel edges, to provide for flow through the interior thereof of a second fluid, e.g., a dialysis fluid for desalting of proteins, amino acids, and/or other biological substances for contact with the liquid flowed through the liquid flow sub-channels and in contact with the main face surfaces of such sintered plate. It will be appreciated that the use of a sintered plate or other porous matrix article may, depending on the performance and dimensional characteristics of the porous structure, obviate the need for separate filter sheet articles. In other words, it may be feasible in some instances to utilize a sintered plate or other porous matrix article as the filter element in lieu of a separate support article associated with discrete filter sheets.

It may be desirable in some instances to form a filter element comprising a core or frame structure which is utilized to impart structural integrity to the filter element, with the core being coated by, affixed to, or otherwise associated with a sintered or cast porous matrix, providing a porous medium for permeate filtration and channeling. Such a core and porous matrix assembly may be unitarily formed by deposition techniques such as chemical vapor deposition, plasma coating, etc. The resulting porous matrix may have any suitable porosity and pore diameter characteristics, as may be necessary or desirable in the given application in which the filter element is employed.

Figure 6:
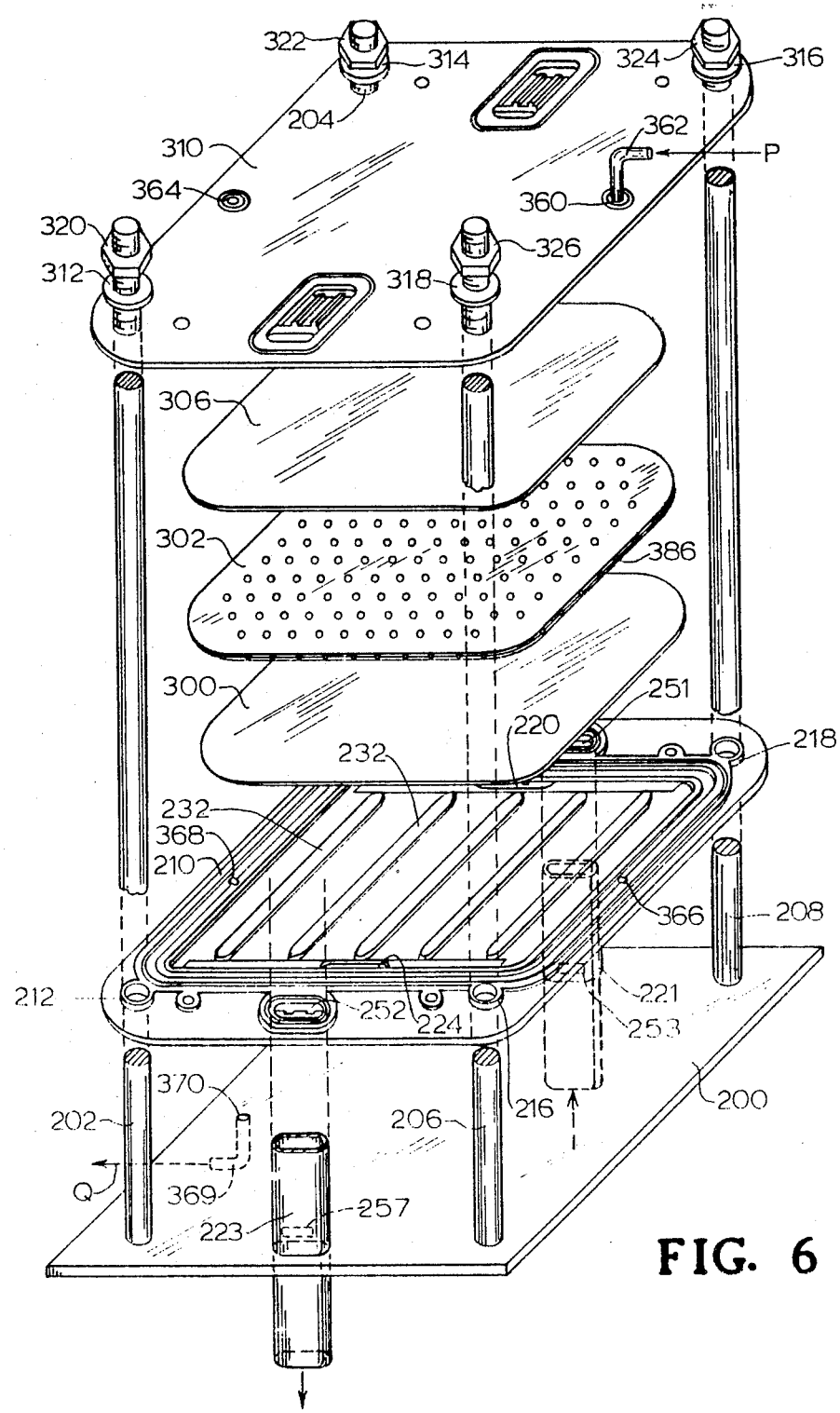
FIG. 6 is an exploded perspective view of a stacked plate filter assembly according to the present invention, showing the details of construction thereof.

FIG. 6 shows an exploded, perspective view of a stacked plate filter according to the present invention, as disposed on a base comprising a mounting plate 200 having vertically upwardly extending rods 202, 204, 206, and 208 at its respective corner portions, as shown. Mounted on the base as a lowermost element of the stack, is a filter plate 210 of the type shown in FIGS. 1-3. The respective rods 202, 206, and 208 extend through the circular openings in the plate which are surrounded by the respective cylindrical flanges 212, 216, and 218 (a similar flanged opening, not visible in this view, is provided for rod 204). The liquid feed conduit 221 for the filter extends through an opening in the base plate 200 and through the liquid inlet opening 251 of the plate member, so that when filter plate 210 is in position, the liquid feed opening 253 is in register with the liquid inlet opening 251 and liquid inlet port 220 of the filter plate.

In like manner, the liquid withdrawal conduit 223 extends through a corresponding opening in the base plate 200 and liquid outlet opening 252, whereby the liquid discharge opening 257 in conduit 223 is brought into register with liquid outlet port 224 when the bottom filter plate 210 is properly positioned.

Reposed on the upper bearing surfaces of the partition walls 232 of the bottom filter plate is a filter sheet 300. The filter sheet may be a paper filter sheet, comprising a non-woven web of cellulosic fibers, or any other replaceable or disposable filtration medium commonly provided in sheet form and which is readily cut or otherwise shaped to the form required in the filter of the present invention. A particularly advantageous filter sheet in filter systems of the type envisioned by the present invention are polysulfone filter sheets which are readily commercially available.

Overlying the filter sheet 300 is the foraminous support 302, which is of the form illustratively shown and described with reference to FIGS. 4–5 herein. Overlying the foraminous support 302 is filter sheet 306, which may be identical in shape and construction to filter sheet 300.

Overlying the upper filter sheet 306 is a filter plate 310 according to the present invention, of identical construction to lower plate 210 but positionally inverted with respect to the lower plate, to form interior sub-channels for liquid flow which are configured as shown in FIG. 7 when the stacked filter plate assembly of FIG. 6 is fully mated with respect to its constituent elements.

As shown, the upper filter plate 310 is configured with openings 364 and 360 communicating wiht the circumscribing channel (see FIGS. 2 and 3, showing the channel as disposed between bounding walls 42 and 16) sorrounding the main flow channel on the plate. Opening 364 in this configuration is closed by a suitable plug, while opening 360 has a fluid introduction passage 362 in flow communication therewith, for feeding of a second liquid, e.g., dialysate solution, into the circumscribing channel (the direction of liquid feeding being indicated by the arrow P). From the circumscribing channel, the liquid enters the foraminous support through the edge openings 386 thereof and flows therethrough to the opposite side of the lower filter plate and into thee circumscribing channel of the lower plate for discharge through openings 368 and 370 and out of the system through the fluid discharge passage 369 in the direction indicated by arrow Q. Circumscribing channel opening 366 of the lower filter plate is closed by a suitable plug in this arrangement.

The stacked filter plate assembly may be retained on the rods 202, 204, 206, and 208 by suitable mechanical fasteners, such as washers 312, 314, 316, and 318, and respective lock-nuts 320, 322, 324, and 326. For such purpose, the rods 202, 204, 206, and 208 are suitably configured with threaded outer surfaces.

It will be apparent from the foregoing that respective sections of stacked plates may be variously joined in fluid flow communication with one another in series to form stacked filter "trains" whose constituent sections may be employed to carry out a number of unit operations on an influent or feed material, such as concentrating (dewatering), washing, dialyzing, desalting, etc.

For example, a stacked filter train of series-connected sections may be employed in a culturing system of the type disclosed and claimed in my copending patent applications U.S. Ser. No. 06/936,486 filed Nov. 26, 1986, and U.S. Ser. No. 07/207,655 filed June 21, 1988, the disclosures of which are hereby incorporated by reference, in applications such as the production in vitro of human immunodeficiency virus (HIV) on cellular or synthetic substrates. In such HIV production application, a first stacked plate section could be employed to concentrate HIV, a second section could be utilized to add media to withdraw media from the system, all without withdrawing any virus, such as might otherwise present a risk of immunosuppressive infection. Thus, a closed system virus culturing arrangement is provided, which is highly advantageous not only for the production of HIV but also the culturing or other processing of pathogenic as well as non-pathogenic bacterial, viral, and yeast species.

Figure 8:
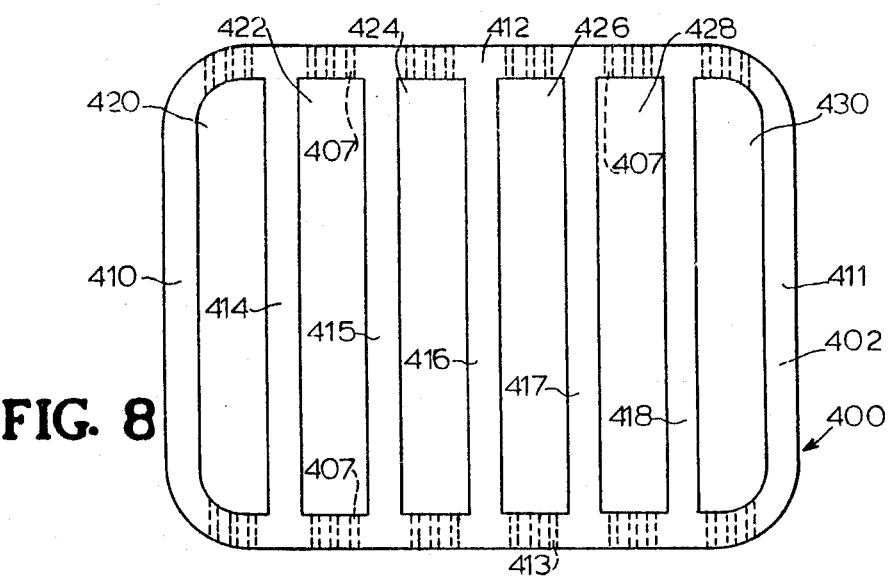
FIG. 8 is a plan view of a support for a unitary filter element assembly according to the invention.

FIG. 8 is a plan view of a support for a unitary filter element. The support 400 includes a circumscribing frame 402 formed by the respective side portions 410, 411, 412, and 413. The circumscribing frame is associated with an array of spaced-apart and substantially parallelly aligned ribs 414, 415, 416, 417 and 418 extending between and joined at their opposite ends to the frame (sides 412 and 413, respectively). The ribs and frame thus corporately form a series of corresponding substantially parallel filtrate flow channels 420, 422, 424, 426, 428 and 430, as shown. Openings 407 are provided in the frame in liquid flow communication with the filtrate flow channels for egress of filtrate from the filtrate flow channels through the frame openings.

Figure 9:
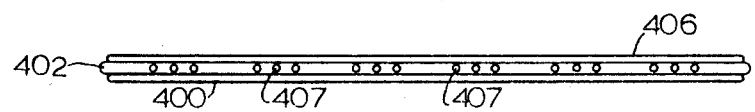
FIG. 9 is an edge elevation view of a unitary filter element assembly comprising the support shown in FIG. 8.
Figure 10:
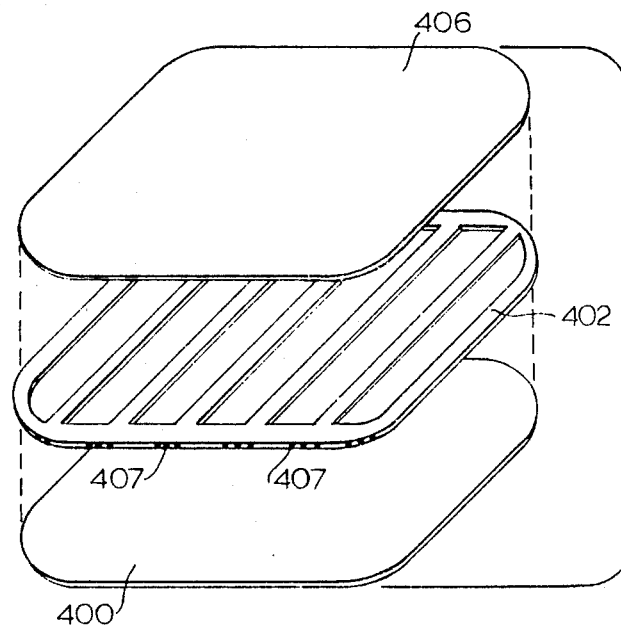
FIG. 10 is an exploded perspective view of the filter unitary filter element assembly shown in FIG. 9, illustrating the arrangement of its constituent parts.

FIG. 9 is an edge elevational view of the filter element comprising the support shown in FIG. 8. FIG. 10 is an exploded perspective view of the unitary filter element whose edge elevational view is shown in FIG. 9.

As shown in FIGS. 9 and 10, the unitary filter element features a first filter sheet 406 which is suitably secured, either continuously or intermittently, along its margins to a first face of the frame 402. Likewise, a second filter sheet 400 is suitably secured along its margins to a second face of the frame. When thus assembled, the first and second filter sheets together with the frame define an enclosed interior volume comprising the filtrate flow channels separated by the ribs. Accordingly, filtrate entering the enclosed liquid volume through the first and second filter sheets, i.e., by permeation of liquid through the filter sheets, may flow in the filtrate flow channels and be discharged from the filter elements through the frame openings 407 which are in liquid flow communication with the filtrate flow channels.

The above-described unitary filter element may suitably be constructed and employed for short term filtration operation, e.g., on the order of about 6 months, following which the filter element may be discarded and replaced with a corresponding new element.

The unitary filter element may be formed of any suitable materials, such as for example polysulfone, polyvinyl chloride, polycarbonate, polyimide, cellulose acetate, cellulose triacetate, mixed esters of cellulose, polyvinylidene difluoride, polypropylene, nitrocellulose, polyethylene, and the like, as may be useful in the desired end use filtration application. The first and second filter sheets may be suitably secured, either continuously or intermittently, along their margins to the respective first and second faces of the frame by any suitable joining or attachment method, including, but not limited to, ultrasonic welding, heat sealing, solvent welding, and adhesive bonding, as well as mechanical affixation.

In lieu of the filter element support illustratively shown and described with reference to FIGS. 8–10 hereof, it may be advantageous in some applications to utilize a flat planar element of appropriate size and shape on the faces of which are provided a series of parallelly aligned, laterally spaced-apart grooves. These grooves may for example each have a cross-section of V-shape in lateral cross-section. Such grooves serve as permeate channels when the support is associated with respective filter sheets disposed on its main facial surfaces. It will be recognized that other cross-sectional shapes for the grooves may be suitably employed for such purpose.

As an alternative to the provision of such grooves, it may be desirable in some instances to utilize a generally planar support element having a series of parallelly aligned, laterally spaced-apart ridges or protrusions on the main facial surfaces of the element.

It will be apparent from the preceding description that any number of paired filter plates, with interposed filter elements, may be assembled to form a cross-flow filter. The number of stacked filter plates in a specific filter system will be largely determined by space requirements and constraints, allowable pressure drop in the system, solids concentration and volumetric flow rate of the liquid to be filtered, and the filtration efficiency of the specific filter sheets employed.

In an illustrative commercial embodiment having the dimensions for the filter plates previously described in connection with FIGS. 1–3 hereof, a superficial velocity of aqueous biomass suspension in the range of 1.5 meters per second through the flow channel defined between adjacent paired plates is readily accommodated, at a volumetric feed rate of approximately 1 liter of aqueous biomass suspension per minute in the flow channel, without any significant maldistribution of the liquid flow therein.

With the partitioned sub-channel structure of the flow channel between adjacent filter plates in the cross-flow filter of the invention described hereinabove, the influent liquid is distributed by the liquid feed trough so that substantially equal amounts of liquid are passed into each of the transversely spaced-apart sub-channels between adjacent plates.

An analogous construction of the liquid collection trough at the opposite end of the flow channel provides a corresponding uniform collection of solids-depleted liquid after contacting of the solids-containing liquid with the filter sheet media.

The filter assembly comprising filter plates of the present invention is highly hydraulically uniform in operation, without the existence of operational tendencies toward flow anomalies, such as bypassing, channeling, and "dead space" formations, which are found in stacked plate filters of the prior art. Accordingly, the stacked plate filter assembly of the present invention achieves a substantial advance in the art, which permits the full areal extent of the filter sheet media to be efficiently employed for solids-liquid separation. In consequence, filter assemblies according to the invention are capable of extended operation relative to the on-stream operating periods characteristics of prior art filters, before regeneration or drainage and replacement of filter elements is necessary.

Figure 11:
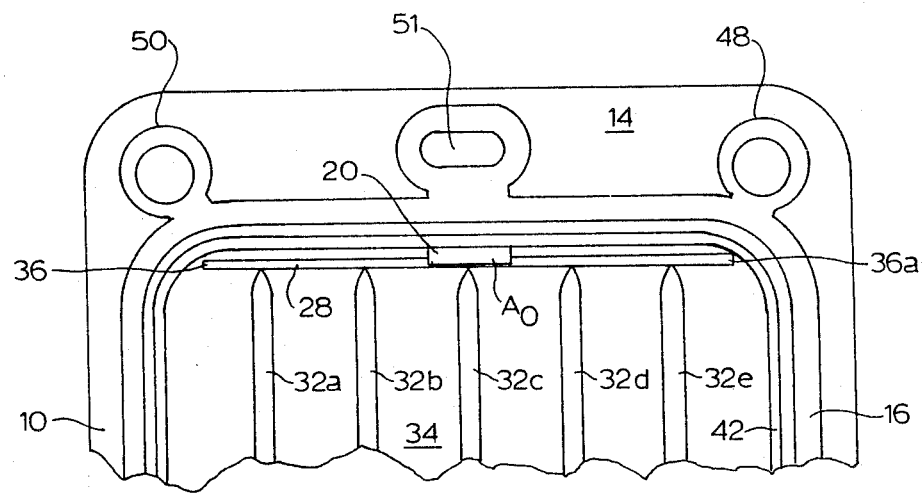
FIG. 11 is a top plan view of a filter plate of the type which is fully shown in FIG. 1, indicating the open area of the liquid inlet port.

FIG. 11, shows a portion, in top plan view, of a filter plate of the type which is fully shown in FIG. 1, and correspondingly numbered with respect to the earlier drawing. As previously described, the opening 51 is provided to accommodate a liquid feed conduit serving to introduce liquid to the flow channels defined by adjacently paired stack plates. For such purpose, the liquid feed conduit is provided with an opening in register with the liquid inlet opening 51 of the filter plate, as shown and described with reference to FIG. 6 hereof.

Liquid inlet opening 51 is in liquid flow communication with liquid inlet port 20, by means of which the influent liquid stream to be filtered is introduced into the liquid feed trough 28 for flow across the plate in the sub-channels defined by partitions 32a–32e. For ease of reference in the ensuing discussion, the open area of the liquid inlet port 20 has been designated in FIG. 11 as represented by the symbol $A_o$. The area $A_o$ of the liquid inlet port is measured in the plane of the plate 10, as shown in the top plan view of FIG. 11.

Figure 12:
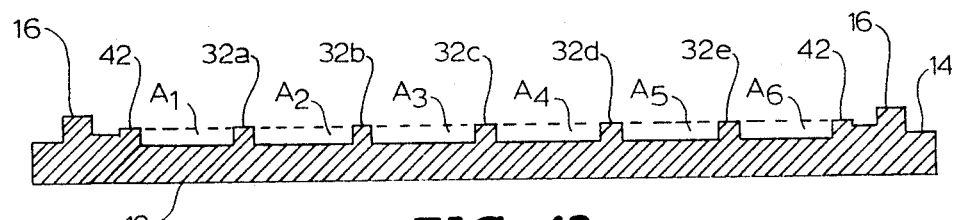
FIG. 12 is a transverse sectional elevation view of the filter plate of FIG. 11, showing the cross-sectional area characteristics of the sub-channels associated with such filter plate.

FIG. 12 is a transverse sectional elevational view of the filter plate of FIG. 11, wherein the constituent elements have been numbered correspondingly with reference to FIG. 11 and FIG. 3 hereof. The partitions 32a–32e define a series of sub-channels extending longitudinally between the liquid feed trough and the liquid collection trough as previously described. These partitions are of a height generally co-extensive with the height of interior circumscribing wall 42, whereby the filter element may be supportively reposed on the upper flat surfaces of the interior circumscribing wall and the sub-channel partitions. In this fashion, there are provided transversely successive flow channels whose cross-sectional areas in a plane perpendicular to the longitudinal axis of the flow channels are denoted $A_1$, $A_2$, $A_3$, $A_4$, $A_5$, and $A_6$, for the six respective sub-channels shown in FIG. 12.

It has been discovered that a critical relationship exists between liquid inlet port open area, $A_o$, and the sum of the open areas of the liquid flow sub-channels, wherein i is an integer denoting the specific sub-channel, and n equals the total number of such sub-channels. If the summation of the separate cross-s of the transversely successive sub-channels, is denoted as $A_s$, the relationship which has ben discovered to be desirable for effective operation of the plate, is of the following form:

$$A_o = y \times Z_s$$

wherein y has a value of from about 0.8 to about 1.3. It has been found that as long as $A_o$ has this relationship to $A_s$, no significant bypassing of influent liquid occurs in the flow channel. Preferably, $A_o$ is equal to $A_s$.

Thus, in a plate wherein the liquid inlet port open area $A_o$ is 3/16 square inch, corresponding to a liquid inlet port having a transverse dimension of ¾ inch and a longitudinal dimension (parallel to the direction of flow of liquid in the flow channels) of ¼ inch, and wherein each of the six liquid sub-channels has a transverse dimension of approximately 0.9 inch and a height of 1 millimeter, the degree of liquid bypassing is very small, as a result of the areal ratio $A_o/A_s$ being approximately 0.87.

In general, it has been discovered that if $A_o$ gets too large relative to $A_s$, there is a tendency to obtain false pressure readings for liquid pressure conditions inside the stacked plate filter. Typically, an external pressure tap is employed with associated meter, gauge or other output indicating means, and the external pressure is utilized to indicate the internal pressure conditions exisiting in the stacked plate assembly. When $A_o$ is significantly larger than $A_s$, viz., above about 1.3 times the value of $A_s$, the external pressure readings tend to falsely indicate the internal pressures. Further, if $A_o$ becomes substantially greater than about 1.3 times $A_s$, and the influent liquid pumping rate is moderate to high in magnitude, the Reynolds number of the influent liquid flow stream increases disproportionately and flow anomalies and other adverse flow phenomena occur, due to channeling and inlet effects.

If, on the other hand, the liquid inlet port area $A_o$ is too small in magnitude relative to the aggregate subchannel cross-sectional area $A_s$, then bypassing is prone to occur on the filter plate. Thus, $A_o$ should not be significantly less than about 0.8 times the magnitude of $A_s$.

More preferably, $A_o$ should be within about 10% of the magnitude of $A_s$, i.e., the cross-sectional area ratio $A_o/A_s$ should be from about 0.9 to about 1.1.

Figure 13:
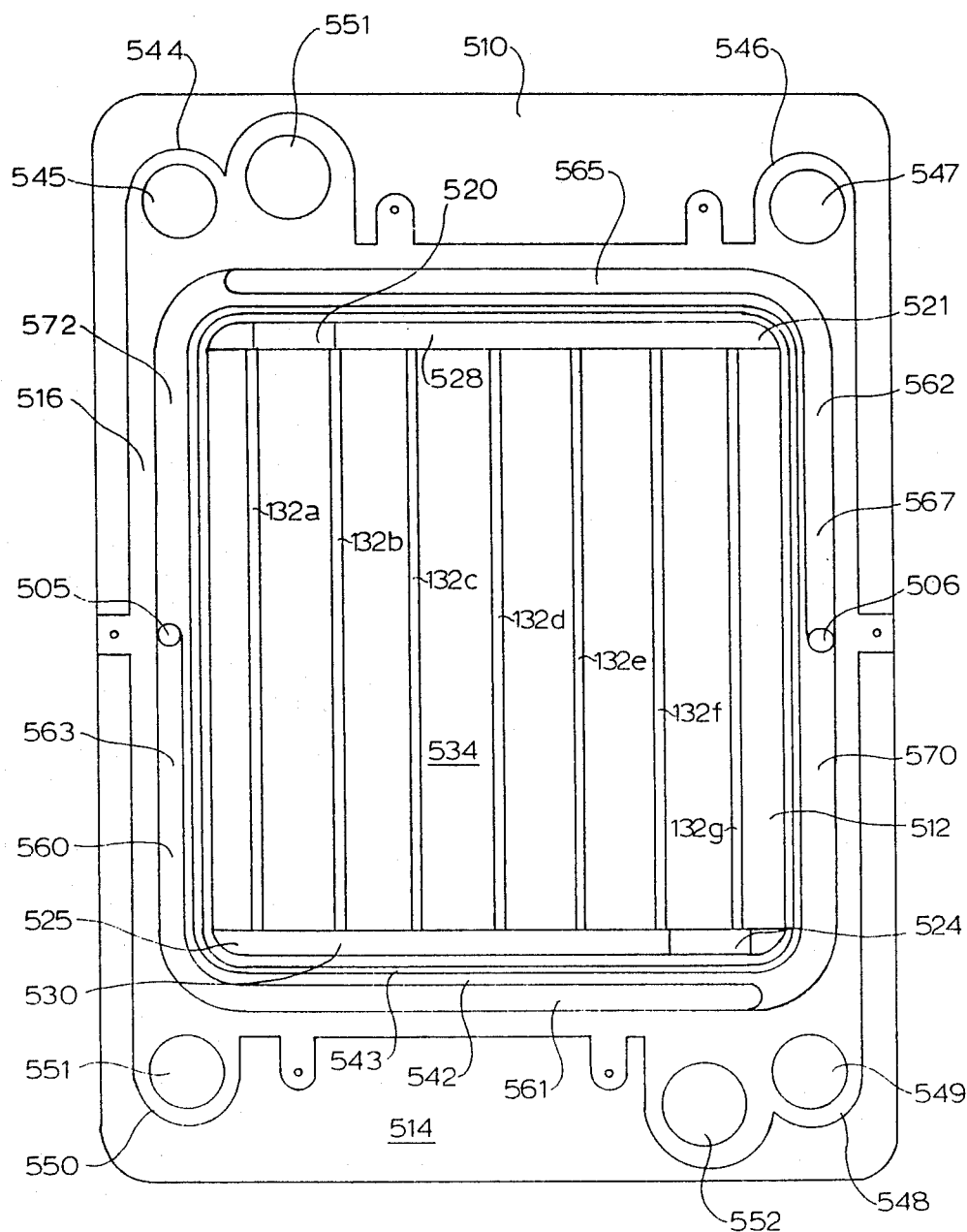
FIG. 13 is a top plan view of a filter plate according to another embodiment of the present invention.

FIG. 13 is a top plan view of a filter plate according to another embodiment of the present invention. The plate member 510 is generally planar, or flat, in construction, and may have the rectangular shape shown, comprising a square-shaped flow channel 512. It is to be appreciated, however, that the filter plates in accordance with the present invention may have any other suitable shape and geometry. For example, the plate may comprise a square or rectangular flow channel, surrounded by a corresponding quadrilateral or other shaped plate, e.g., circular or oblong, as may be advantageous in a given application. Preferably, however, the plate member is of substantially rectangular shape, and the flow channel has a generally square shape, when the plate is viewed in top plan view.

As in previously described embodiments, the plate member 510 has a substantially flat bottom surface, and a top surface 514 which is substantially flat in the peripheral portions of the plate. The top surface 514 has a first, outer wall 516 circumscribingly bounding the flow channel and upwardly extending from the top surface 514 of the plate member.

The first outer bounding wall 516 of the plate comprises integral flange sections 544, 546, 548, and 550, which extend longitudinally at the four corners of the outer circumscribing wall. These flange sections contain circular openings 545, 547, 549, and 551, respectively, which accommodate the positioning of the plate on spaced-apart rods, as previously described with reference to FIG. 6 hereof. The diagonally opposite flange sections 544 and 548 also comprise respective liquid inlet and liquid outlet openings 551 and 552, which mate cooperatively with liquid feed and liquid discharge conduits, similar to the arrangement described with reference to FIG. 6 hereof.

Plate 510 is also provided with a second, inner circumscribing wall 542, of lesser height than the first outer wall 516. In this fashion, inner wall 542, which extends upwardly from the plate top surface, interiorly bounds the liquid flow channel 512. Along its top surface, the inner bounding wall 542 is provided with a groove in which is disposed a gasket element 543, to insure positive liquid-tight sealing of the plate against the filter element disposed between adjacent paired plates. The gasket may be formed of any suitable material which is satisfactory in the intended service of the filter plate to provide fluid sealing and to withstand the operating, regeneration, and sterilization conditions to which the filter comprising the plate may be exposed, without loss of sealing capability.

The second, inner circumscribing wall 542 is in spaced relationship to the outer wall 516 along diagonally opposed L-shaped peripheral sections of the flow channel, to form respective L-shaped peripheral channels 560 and 562 between the inner and outer circumscribing walls. The L-shaped channel 560 comprises a leg 561 extending transversely across the flow channel for a major portion of the length thereof, and a leg 563 extending longitudinally for a portion of the longitudinal dimension of the flow channel, communicating at its extremity with an opening 505 extending through the plate. The L-shaped peripheral channel 562 likewise comprises a leg 565 extending transversely across the flow channel for a major portion of the length thereof, and a leg 567 extending longitudinally for a portion of the longitudinal dimension of the flow channel and communicating at its extremity with an opening 506 extending through the plate. The portions of the periphery of the flow channel not comprising such L-shaped sections comprise ridge elements extending between the inner and outer circumscribingly bounding walls. Thus, the inner wall 542 extends transversely to the outer bounding wall on the right hand side of the plate as shown in FIG. 13, to provide the ridge 570. In like manner, the inner bounding wall extends transversely to the outer wall on the left hand side of the plate as shown, forming the ridge 572. In such fashion, the diagonally opposite L-shaped channels are bounded at their extremities by the respective ridges.

In this plate, a liquid inlet port 520 is provided at the upper left-hand corner of the plate as shown in FIG. 13, and a liquid outlet port 524 is correspondingly provided at a lower right-hand corner of the flow channel, i.e., diagonally opposite the inlet port.

The liquid inlet 520 is joined in a liquid flow communication with liquid inlet opening 551, and the liquid outlet port 524 likewise is joined in liquid flow communication with the liquid outlet opening 552. The liquid inlet port 520 also is joined in liquid flow communication with a liquid feed trough 528 extending transversely across a first side of the flow channel. Corresponding, the liquid outlet port 524 is joined in liquid flow communication with a liquid collection trough 530 extending transversely across a second side of the flow channel, longitudinally spaced from the liquid feed trough.

A plurality of transversely spaced-apart partitions 132a, 132b, 132c, 132d, 132e, 132f, and 132g, extend upwardly from the floor 534 of the flow channel between the liquid feed trough 528 and the liquid collection trough 530. The partitions 132a–132g are of substantially the same height as the inner circumscribing wall 542. The partitions are parallelly aligned with one another to define a series of sub-channels therebetween, which extend longitudinally between the liquid feed trough and the liquid collection trough.

The liquid feed trough 528 is of progressively decreasing depth, from the vicinity of the liquid inlet port 520, along the transverse direction to its transverse extremity 521. The liquid collection trough 530 likewise is of progressively decreasing depth from the vicinity of the liquid outlet port 524, along the transverse dimension of the trough to its transverse extremity 525. The term "depth" in this context has the same meaning as previously set forth in connection with the description of the filter plate of FIGS. 1–3 hereof.

In the filter plate shown in FIG. 13, the provision of a liquid inlet port 520 whose cross-sectional area is related to the total transverse cross-sectional area of the sub-channels demarcated by partitions 132a–132g, in accordance with the areal ratio ($A_o/A_s$) criteria described hereinabove, provides a highly efficient filtration system, in which uniform flow distribution is provided, so that bypassing is substantially completely eliminated. By this configuration, the interior pressures of the flow streams are equalized, so that liquid flowing transversely in the collection trough 530 and reaching the liquid outlet port 524 has essentially the same pressure as liquid flowing out of the sub-channel bounded by respective partition walls 132f and 132g. As a result of the substantial absence of bypassing, channeling, and other anomalous flow phenomena, the efficiency of the filtration operation is maximized, in that the entire areal extent of the flow channel is utilizable for filtration. Further, this high efficiency filtration is achievable, for streams which do not require turbulent flow and which do not form gel layers, utilizing low Reynolds number conditions, e.g., a Reynolds number of 1,000 or even lower.

Figure 14:
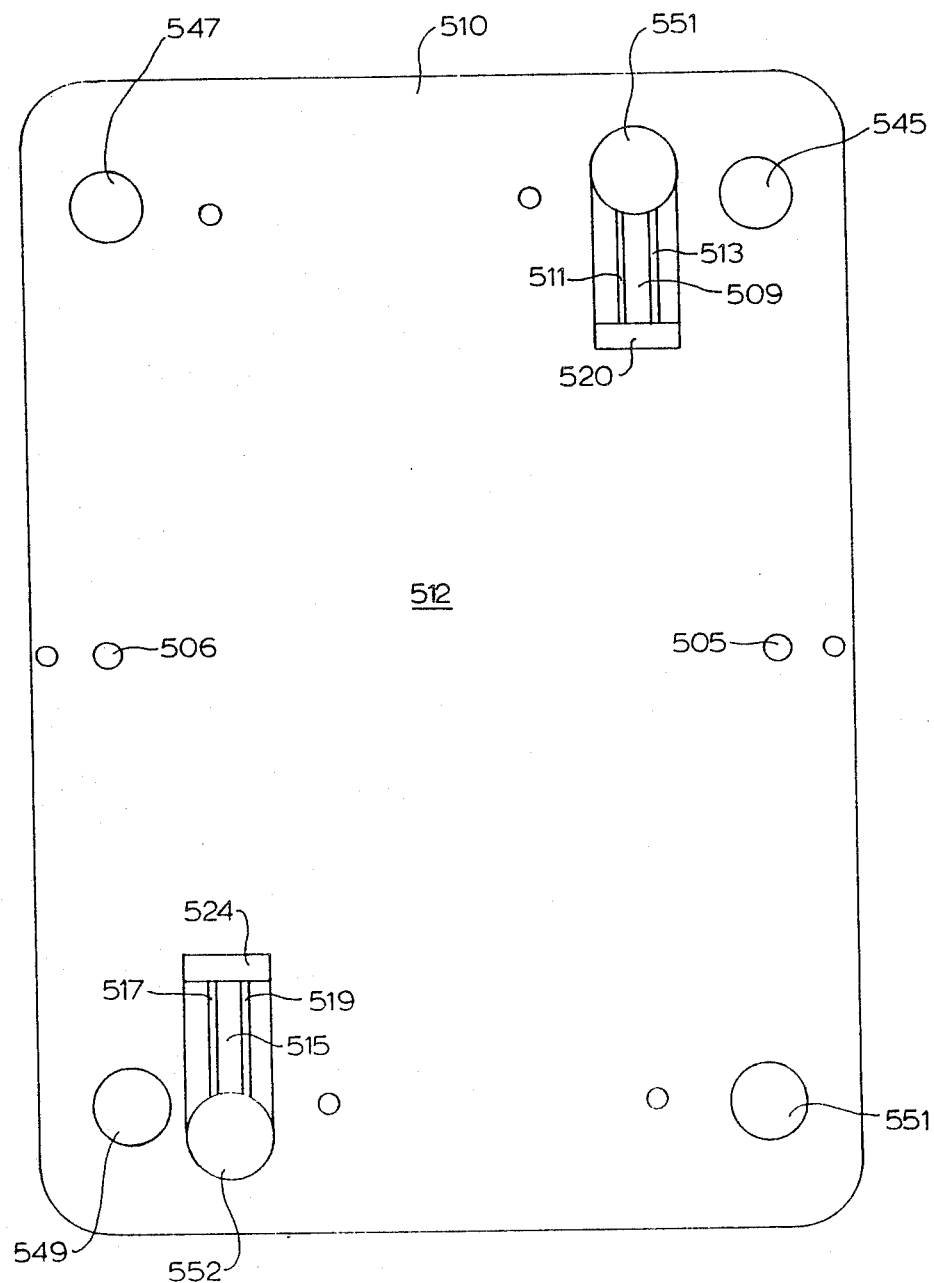
FIG. 14 is a bottom plan view of the filter plate of FIG. 13.

FIG. 14 is a bottom plan view of filter plate 10 shown and described with reference to FIG. 13. The filter plate as shown in FIG. 14 features a flat bottom surface 512, and at the corner portions of the plate there are provided the previously described openings 545, 547, 549, and 551, for mounting of the plate on rods to form a stacked plate assembly. The liquid inlet opening 551 is shown as communicating with the liquid inlet port 520 via a liquid feed channel 509 comprising flow divider partitions 511 and 513, to provide for uniformity of flow entering the liquid inlet port 520 from the flow channel.

Correspondingly, the liquid outlet opening is shown as being in liquid flow communication with the liquid outlet port 524 via the liquid discharge channel 515. In the liquid discharge channel are disposed flow dividing partitions 517 and 519, to provide uniformity of flow from the liquid outlet port 524 to the liquid outlet opening 552.

Also illustrated are permeate openings 505 and 506 which extend through the plate and communicate with the respective L-shaped channels lying between the inner and outer circumscribing walls bounding the flow channel. In operation, these respective permeate openings may be employed to convey or drain the solids-depleted filtrate liquid or other permeate from the stacked plate assembly, or they may be alternatively utilized in other flow modes, such as those illustratively described hereinabove in connection with the openings 5 and 6 in the plate embodiment of FIGS. 1–3.

Figure 15:
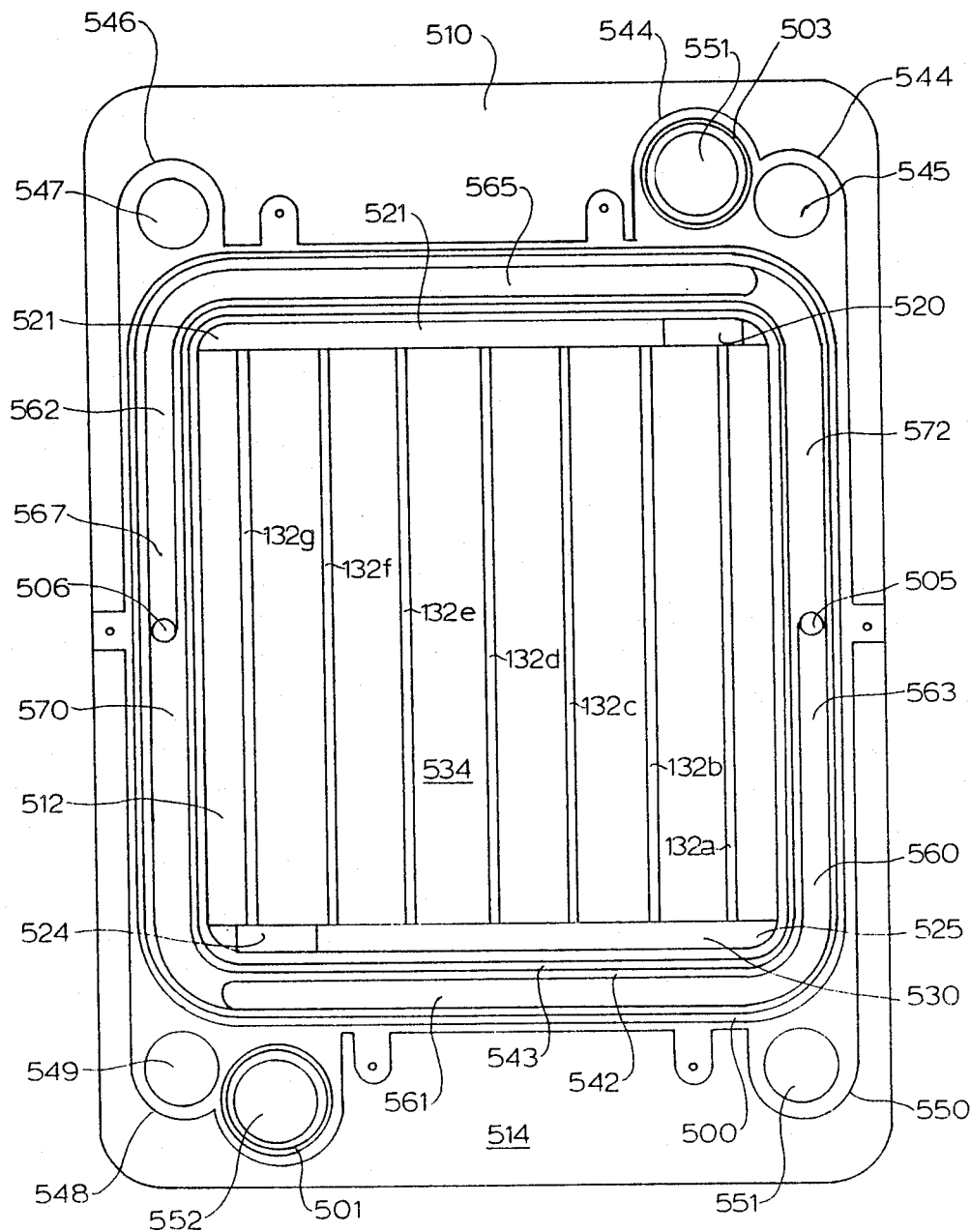
FIG. 15 is a top plan view of a filter plate according to still another embodiment of the present invention.
Figure 16:
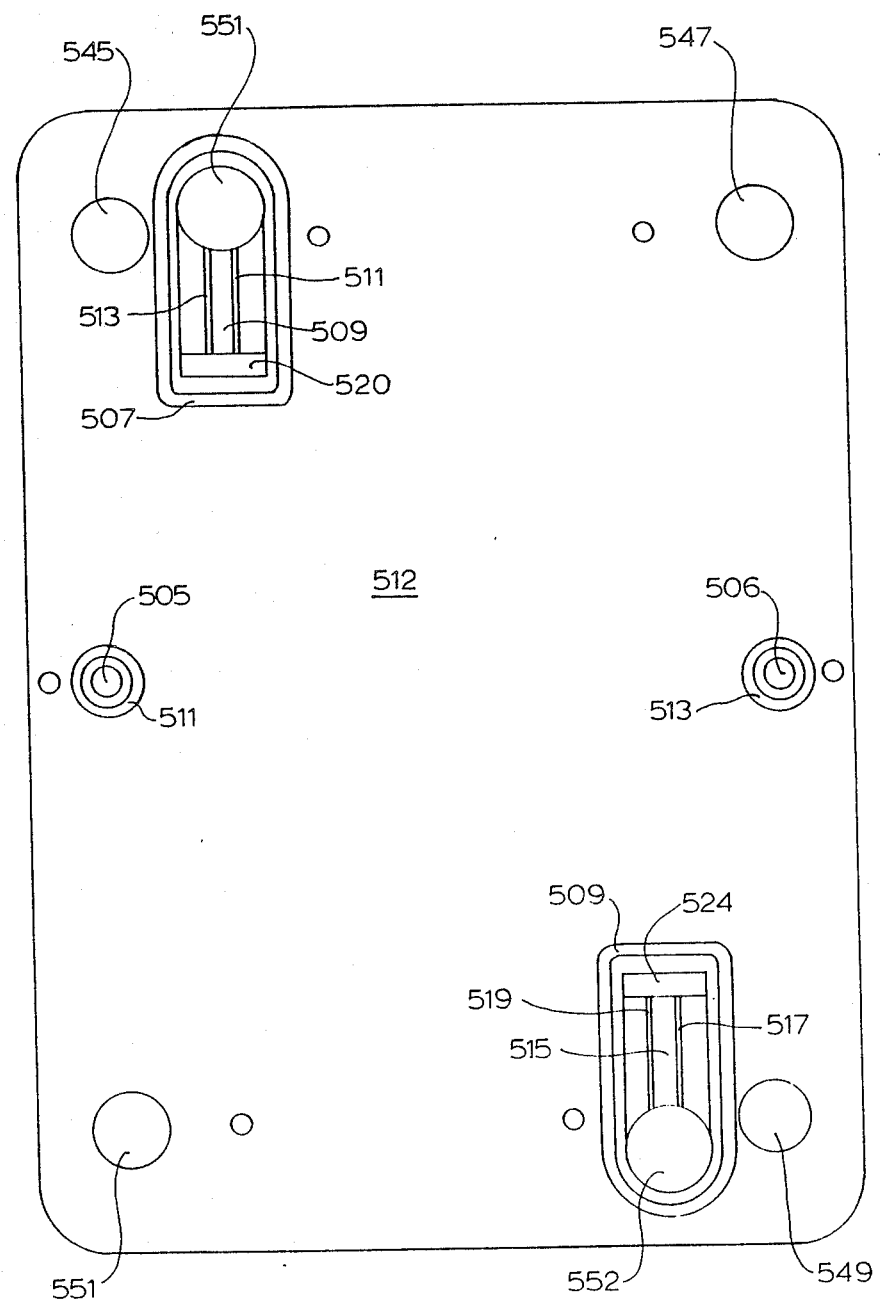
FIG. 16 is a bottom plan view of the filter plate of FIG. 15.

FIG. 15 is a top plan view of a filter plate according to still another embodiment of the invention, and FIG. 16 is a bottom plan view of the same plate, wherein all parts and features are numbered correspondingly with respect to FIGS. 13 and 14.

The plate shown in FIGS. 15 and 16 is symmetrical to, i.e., a mirror-image of, the plate of FIGS. 13 and 14, so as to be matable with the latter, with the respective plates in inverted facing relationship to one another to provide an enclosed flow channel. For purposes of sealing, when the plate of FIGS. 15 and 16 is mated with the plate of FIGS. 13 and 14, the former is provided with a gasket 500 extending peripherally along the entire top surface of the outer circumscribing wall 516. In addition, the flange 544 surrounding the liquid inlet opening 551 is provided on its top surface with a gasket 503 about the periphery of the liquid inlet opening. Similarly, the flange 548 surrounding the liquid outlet opening 552 is provided on its top surface with a gasket 501 about the periphery of outlet opening 552.

With particular reference to FIG. 16, the bottom surface of the plate 512 features suitable recesses accommodating gaskets 507 and 509 around the respective liquid inlet and outlet structures, and gaskets 511 and 513 surrounding the openings 505 and 506, respectively. In this manner, the flat plate surfaces of facing plate pairs in the stack are sealed against one another.

Figure 17:
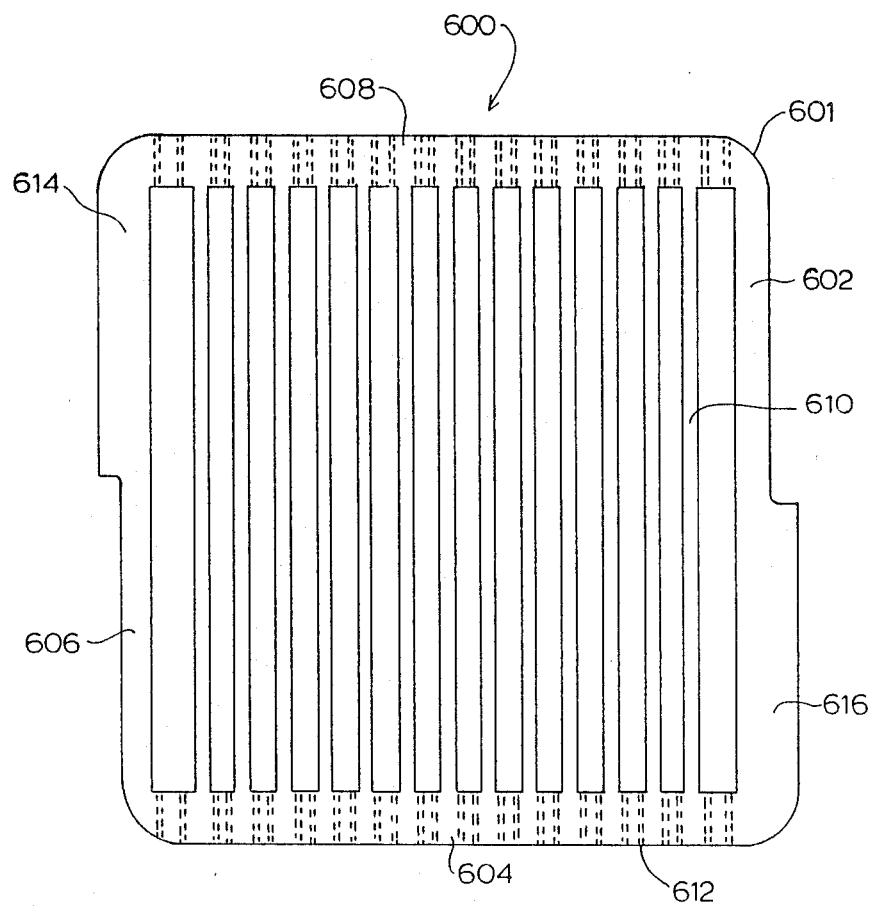
FIG. 17 is a top plan view of a filter element frame, such as may be usefully employed with filter plates of the type shown in FIGS. 13-16.

FIG. 17 is a top plan view of a filter element support 600, such as may be usefully employed with filter plates of the type shown in FIGS. 13–16. This support includes a circumscribing frame 601 formed by the respective side portions 602, 604, 606 and 608. The circumscribing frame has associated therewith an array of spaced-apart and substantially parallelly aligned ribs 610, which extend between and are joined to their opposite ends to the frame (sides 604 and 608, respectively). The ribs and frame thus corporately form a series of corresponding parallel filtrate flow channels. Openings 612 are provided in the frame in liquid flow communication with the filtrate flow channels for egress of filtrate from the filtrate flow channels through the frame openings. The support includes diagonally opposite, longitudinally extending, marginal flange portions 614 and 616, respectively, which are reposable on the corresponding ridges 570 and 572 of the filter plates (see FIGS. 13 and 15), so that the respective L-shaped channels between the inner and outer circumscribing walls are enclosed and "blocked" by the flange portions at their longitudinal extremities communicating with the respective liquid openings 505 and 506 (see FIGS. 13–16).

The support shown in FIG. 17 may suitably have correspondingly shaped sheets of filter paper bonded to the frame at each of the top and bottom faces thereof, in a manner as previously described in connection with the support structure of FIG. 10.

Figure 18:
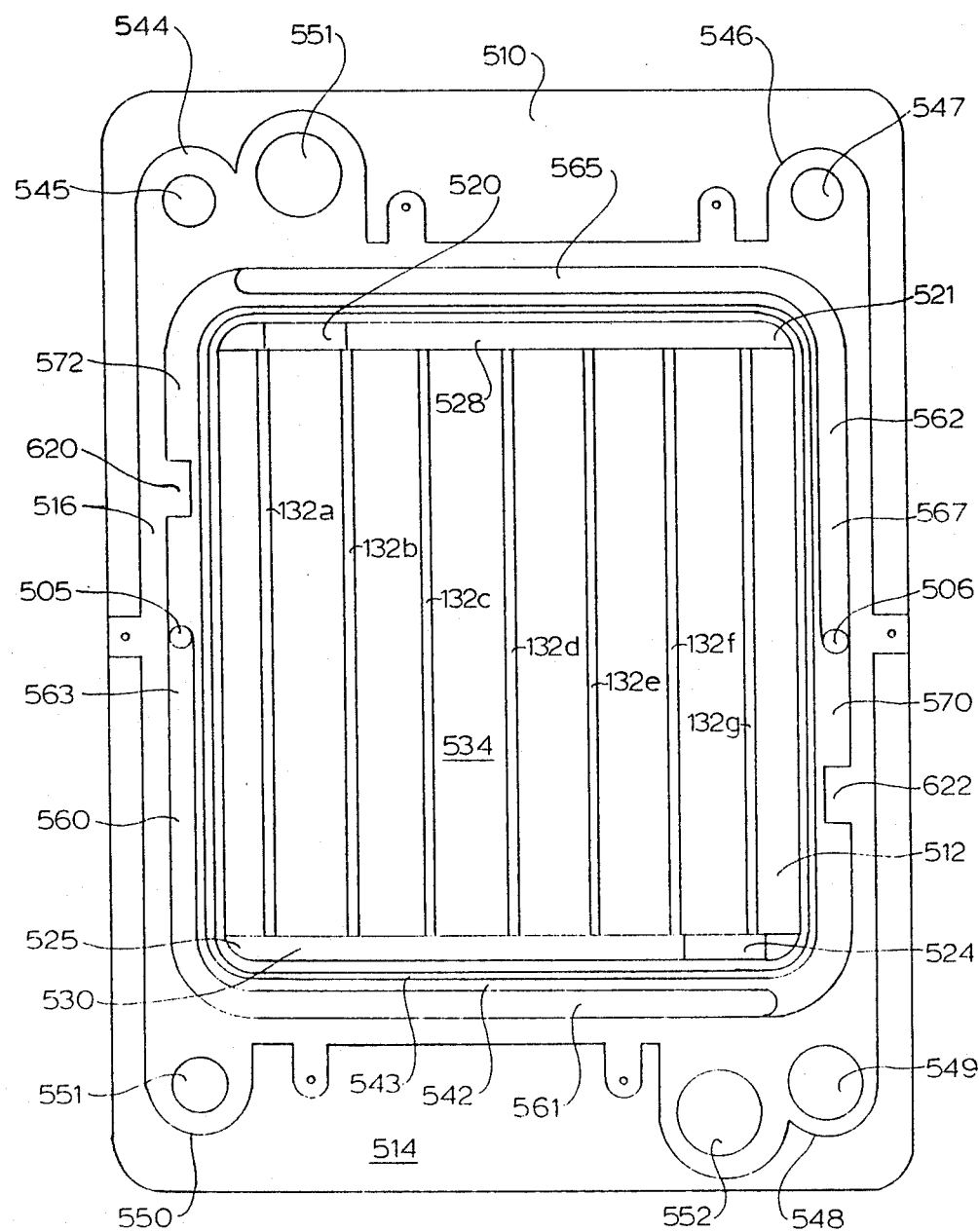
FIG. 18 is a top plan view of a filter plate according to still another embodiment of the present invention.
Figure 19:
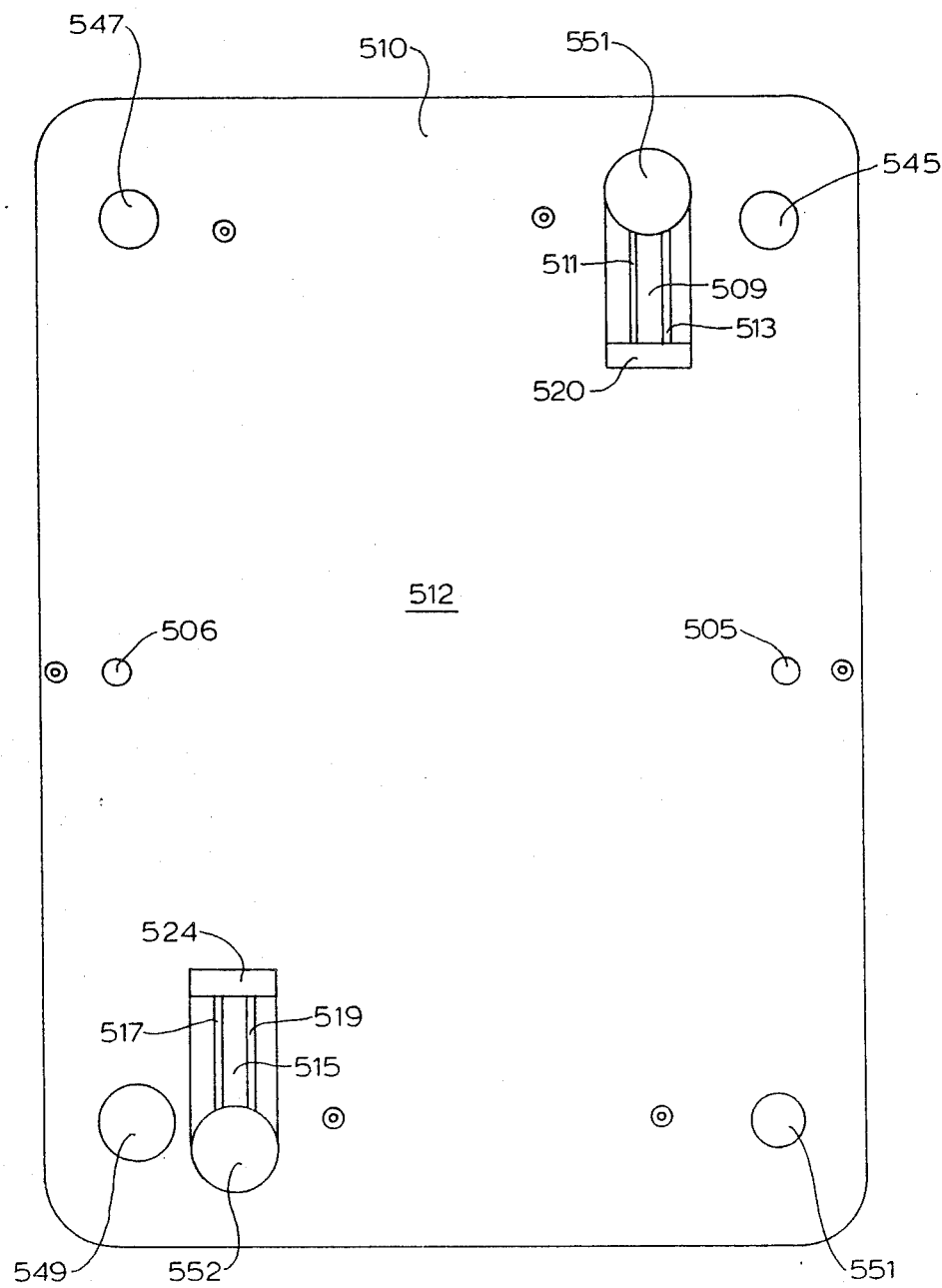
FIG. 19 is a bottom plan view of the filter plate of FIG. 18.
Figure 20:
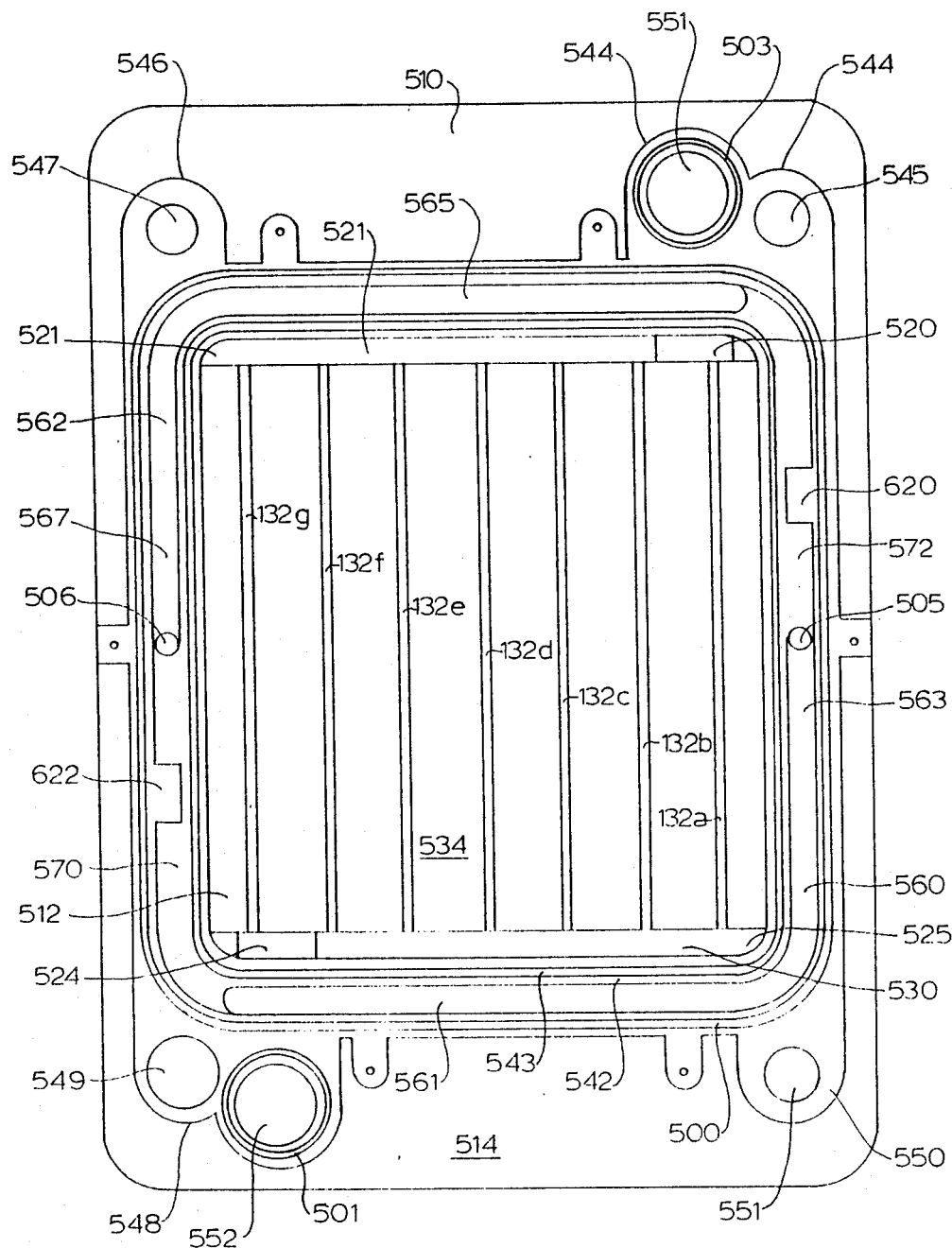
FIG. 20 is a top plan view of a filter plate according to still another embodiment of the present invention.
Figure 21:
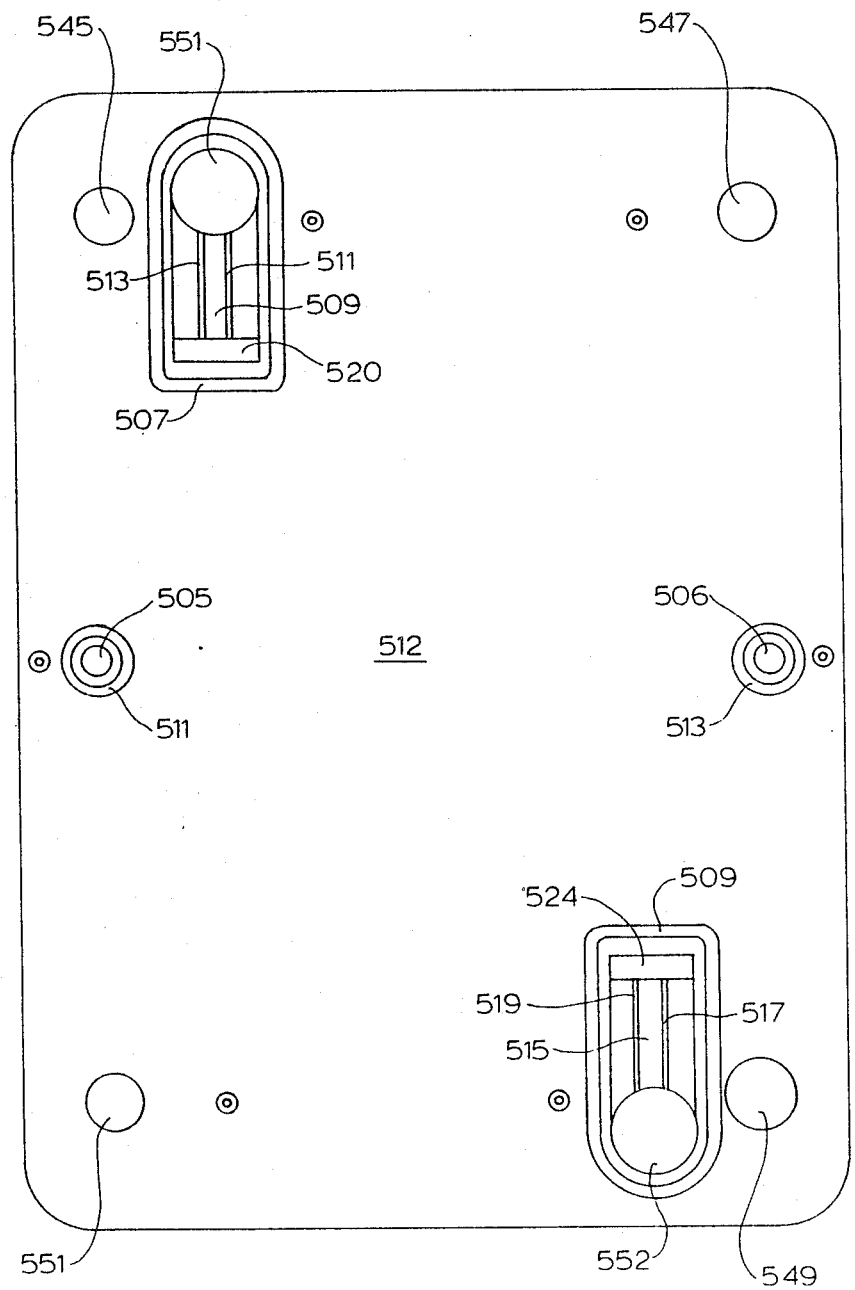
FIG. 21 is a bottom plan view of the filter plate of FIG. 20.

FIGS. 18–21 show filter plates according to a still further embodiment of the invention. FIGS. 18 and 19 representing the top plan and bottom plan views of a first filter plate, and FIGS. 20 and 21 representing top and bottom plan views of a second filter plate which is matable in inverted facing relationship with the plate of FIGS. 18 and 19, to form a paired plate structure enclosing an interior flow channel in the previously described manner. The plates shown in FIGS. 18–21 are numbered correspondingly to the plate of FIGS. 13–17, and are correspondingly formed, with the exception of the filter element keying structure, described below.

By way of background, it will be seen from an inspection of the respective FIGS. 13, 15, and 17, that the filter support shown in FIG. 17, featuring diagonally opposed marginal flanges 614 and 616 is properly positioned for use so that the marginal flanges are supportively resposed against respective ridges 572 and 570. If, however the filter element is "flipped over" relative to the position shown in the plan view of FIG. 17, the marginal flanges will not abut the ridge surfaces of the adjacent plates, but instead the positions of the filter element will result in leakage from the L-shaped channels between the adjacent inner and outer circumscribing walls, so that such L-shaped channels are joined in liquid flow communication with one another.

Such intercommunication of the respective L-shaped channels is particularly disadvantageous when it is desired to utilize the openings 505 and 506 as respective secondary fluid inlet and discharge passages, to flow a secondary fluid through the support for mass transfer contacting with a primary fluid introduced into the flow channel from the liquid inlet port and discharged from the flow channel in the liquid outlet port. Such mass transfer contacting is desirably carried out in applications such as dialysis, desalting of proteins, introduction of nutrients to a biomass suspension deposited on the filter element, and in numerous other applications, but is precluded by intercommunication of the respective L-shaped channels of the filter plates of FIGS. 13-16, when the filter element support shown in FIG. 17 is incorrectly positioned.

To overcome these difficulties incident to the inadvertent "wrong side up" positioning of the filter element on the filter plate, the filter plates shown in FIGS. 18-21 are provided with a first protrusion element 620 extending inwardly from the outer circumscribing wall 516 across the ridge 572, for part of the transverse dimension (width) of the ridge. This protrusion element is of the same height as the outer circumscribing wall 516, and may suitably be integrally formed with the plate, or alternatively the protrusion element may be a separate element which is attached to the plate by adhesive bonding or other suitable means. Diagonally opposite the first protrusion element is a second protrusion element 622, extending transversely inwardly from the outer circumscribing wall for part of the width of the ridge 570.

Although the protrusion elements have been shown as having a generally rectangular shape, and being provided as a diagonally opposite pair, it will be appreciated that the keying element(s) employed with the plate structure may have any other suitable shape, and may be provided in any suitable number. For example, the plate could be formed with only one protrusion element.

Alternatively, in lieu of the male elements shown, it may be advantageous to provide a female keying element as a keying structure on the plate. Further, the keying structure could utilize any of various other keying devices. For example, the marginal flanges 614 and 616 of the support shown in FIG. 17 could be tinted in a color such as blue, with the support being formed of a transparent material such as polyvinyl chloride or polysulfone, and with the ridge of the plate being complementarily tinted with a yellow color, so that proper superpositioning of the support on the plate with the marginal flange overlying the ridge will produce a resulting green color of these superposed regions of the support and plate. Thus, any keying device which is satisfactory to readily visually show the proper positioning of the support on the plate may be satisfactorily be used in the broad practice of the present invention.

Figure 22:
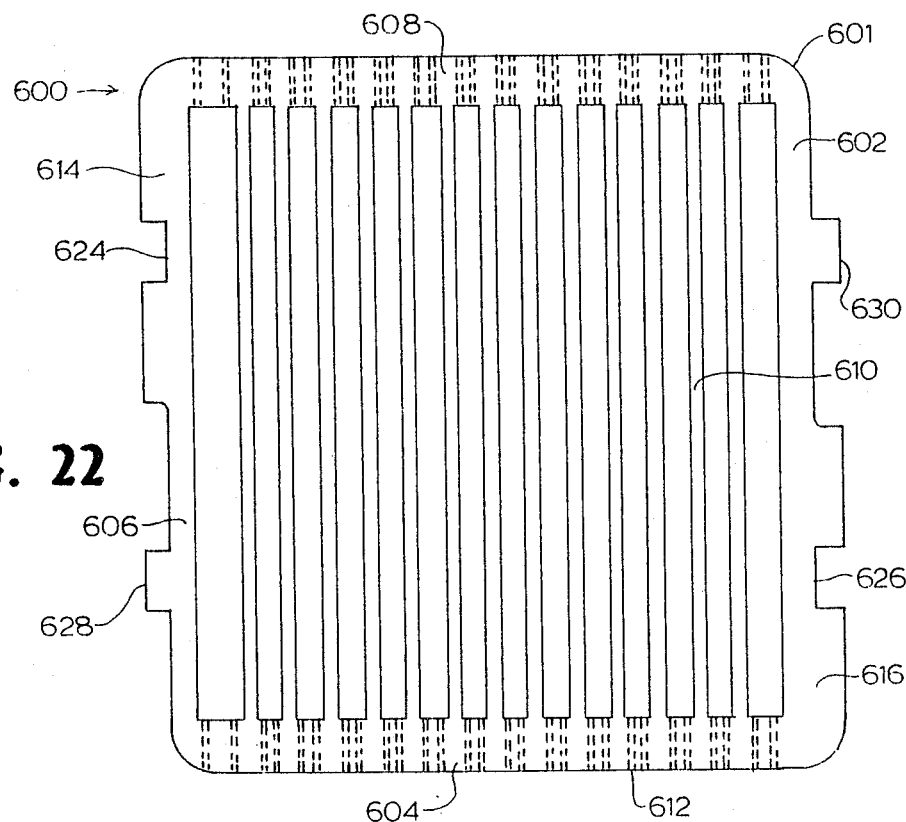
FIG. 22 is a top plan view of a filter element frame according to another embodiment of the invention, such a may be usefully employed with the filter plates shown in FIGS. 18-21.

With reference to the plate filter structures shown in FIGS. 18-21, there is illustrated in FIG. 22 a top plan view of a filter element support, which may be usefully employed with such filter plates.

For ease of description, the support shown in FIG. 22 is numbered correspondingly with reference to FIG. 17, the difference between the two supports being that the respective marginal flanges 614 and 616 in the FIG. 17 embodiment are provided with diagonally opposite flange notches 624 and 626, so that the notch 624 is matable with protrusion 620 (see FIG. 18) and the notch 626 is matable with protrusion 622, when the support is properly positioned. The other difference between the supports shown in FIG. 17 and FIG. 22 is that the non-flanged segments of the side portions 606 and 602 in the FIG. 22 embodiment feature protrusion elements 628 and 630, respectively. Thus, if the support is placed on the filter plate in an improper position, as for example when the support as shown in FIG. 22 is turned over and placed on filter plate 510 as shown in FIG. 18, the support protrusions 628 and 630 will strike plate protrusions 620 and 622, and the support will not properly "seat" on the plate. Thus, the person attempting installation of the support instantly knows, by the non-seating character of the support, that it is improperly positioned, and must be turned over to properly seat, so that the plate protrusions fit into the notches on the marginal flanges of the support.

Figure 23:
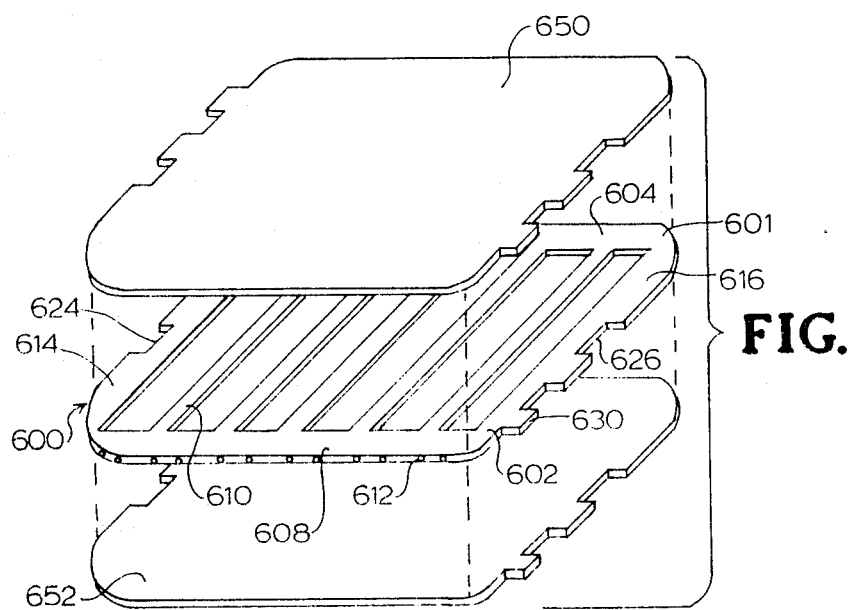
FIG. 23 is an exploded perspective view of the unitary filter element assembly comprising a frame of a type as shown in FIG. 22.

FIG. 23 is an exploded perspective view of a unitary filter element comprising a support of the general type shown in FIG. 22.

This unitary filter element features a first filter sheet 650 which is continuously or intermittently secured along its margins to a first face of the frame 601. Likewise, a second filter sheet 652 is continuously or intermittently secured along its margins to a second face of the frame. When assembled, the first and second filter sheets together with the frame define an enclosed interior volume comprising the filtrate flow channels separated by ribs 610. Thus, filtrate entering the enclosed liquid volume through the first and second filter sheets, by permeation of liquid through the filter sheets, flows in the filtrate flow channels and is discharged the front and rear edges of the frame as shown, through permeate discharge openings 612. In such manner, when the unitary filter element shown in FIG. 23 is positioned in a paired plate assembly comprising the plates shown in FIGS. 18-21, the permeate issuing from the edge openings 612 flows into the respective L-shaped permeate channels for discharge from the plate in openings 505 and 506, respectively.

Figure 24:
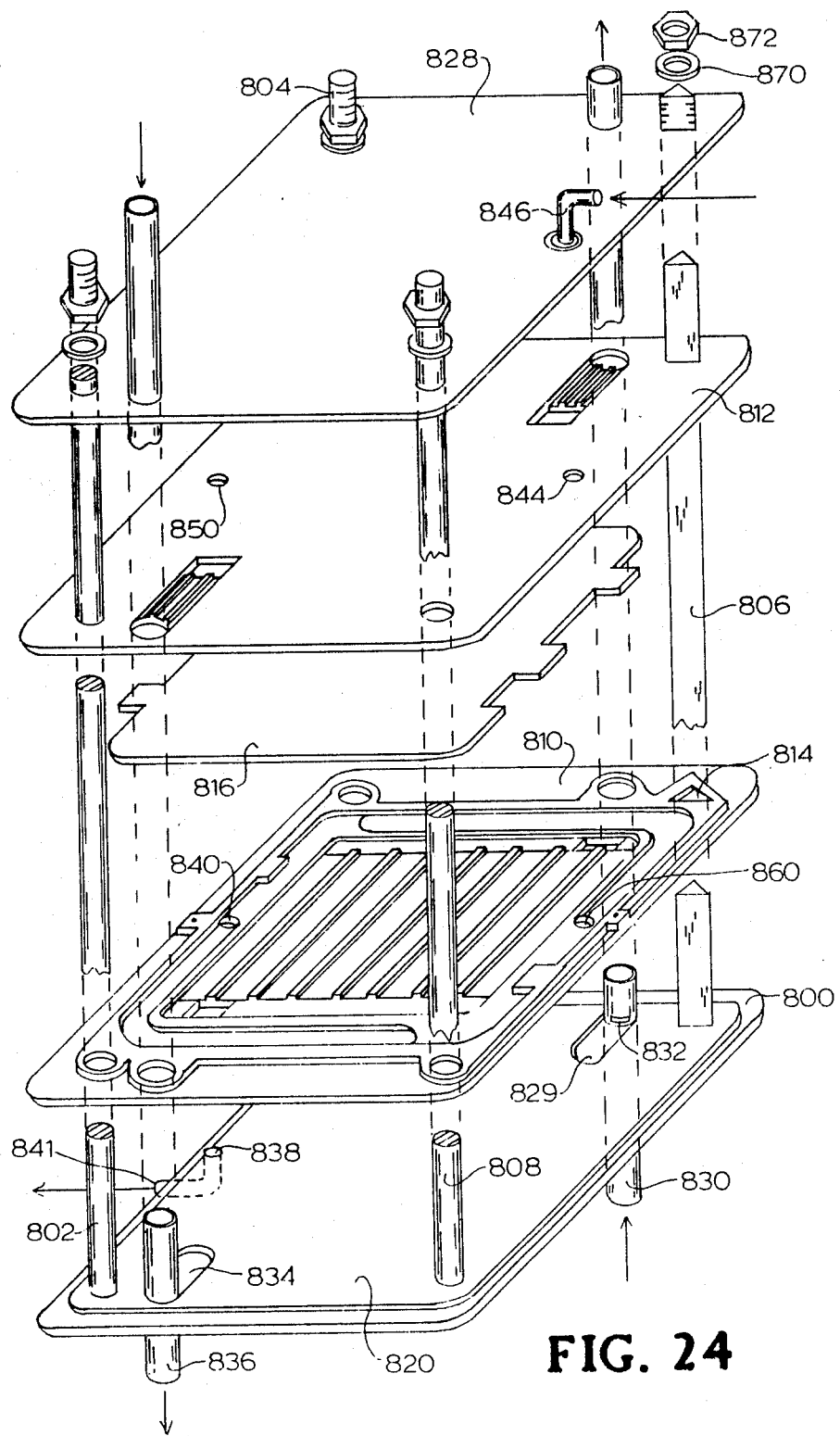
FIG. 24 is an exploded perspective view of a stacked plate filter assembly according to another embodiment of the present invention, showing the details of construction thereof.

FIG. 24 is an exploded perspective view of a stacked plate filter assembly according to another embodiment of the invention, showing the details of construction thereof.

This stacked plate filter is disposed on a base comprising a mounting plate 800 having vertically upwardly extending rods 802, 804, 806, and 808 at its respective corner portions as shown. Each of the rods 802, 804, and 808 are of cylindrical form, having a circular cross-section. The fourth rod 806 is of triangular cross-section. The purpose of the dissimilar cross-sectional shape of rod 806, as compared to the other three rods 802, 804 and 808, is to provide a plate orientation keying structure, which will ensure that the constitutent plates of the filter assembly are assembled in the proper orientation.

Thus, with the plates previously described herein, having circular openings at each of their corner portions to accommodate positioning thereof on cylindrical rods (see FIG. 6), it is possible to mis-register the plates, so that successively pairs are not correspondingly aligned with respect to their liquid inlet and outlet openings. By providing a rod of dissimilar shape, and forming the plates 810 and 812 with triangular openings, such as the triangular opening 814 of plate 810, the proper registration of the plate openings with the proper rods is assured, resulting in correct orientation of the respective stacked plates.

Alternatively, it is possible to configure the rods on which the plates are stacked, with differing diameters. The filter plates then are correspondingly configured with differing sized openings, to ensure proper registration of the plate openings with the proper rods, when the filter plates are stacked to form a filter assembly. For example, in a four-rod assembly, three of the rods may be cylindrical in configuration with a diameter of 5/16 inch, and the remaining rod may be of cylindrial configuration and have a diameter of 7/16 inch.

It may be desirable in some instances to utilize both different shapes and sizes of mounting rods as plate orientation registration means.

It will be appreciated from the foregoing that any other plate orientation registration device may be employed to ensure the correct positioning of the successive stacked plates on the mounting plate 800. For example, the plates may be formed with a notch at one of their side edges, so that all successive plates are oriented with their successive notches superposed with respect to one another. Alternatively, the plate itself may be embossed, etched, or otherwise manufactured with an orientational device, e.g., a raised protrusion in the shape of an arrow, to indicate the correct orientation of the plate when stacked on the mounting plate. In practice, however, the provision of a single rod of differing geometry yields a simple, readily determinable means for ensuring proper positioning of the plates.

Plates 810 and 812 are of the general type illustrated in previously described FIGS. 18-21, except for the provision of a triangular corner opening 814 to accommodate the triangular rod 806, as described above. A unitary filter element 816, of a type as illustratively shown in FIG. 23 hereof, is interposed between the opposed filter plates 810 and 812, which are oriented in inverted facing relationship to one another, so that the respective plates form an enclosed liquid flow channel containing the unitary filter element 816.

Between the lower filter plate 810 and the mounting plate 800, there is provided a sealing gasket 820 which is equipped with openings to accommodate its positioning over the respective rods 802, 804, 806 and 808, so that the gasket seals the bottom flat side of the lower filter plate 810.

As shown, the sealing gasket 820 is provided with an elongate opening 829 accommodating the liquid inlet conduit 830 and the liquid feed channel of the filter plate 810 positioned thereagainst, and in communication with the liquid feed opening 832. Similarly, the gasket 820 features an elongate opening 834 accommodating the liquid withdrawal conduit 836 and the liquid discharge channel of the filter plate 810. Gasket 820 also is provided with an opening 838 communicating with opening 840 of plate 810 and a corresponding opening in the mounting plate 800 to which is joined the secondary fluid outlet 840.

The gasket 820 may be formed of any suitable material which is sealingly effective in the stacked plate filter assembly, such as for example silicone, Buna-N, or EPDM rubber materials, or flexible polymeric materials commercially available under the trademarks Viton ®, Calrez ®, and Teflon ®.

While the stacked plate assembly shown in FIG. 24 is illustrated with only two filter plates according to the present invention, it will be appreciated that the stacked plate assembly may be readily assembled with any selected number of such plates, arranged in appropriate pairs, and operated as desired to provide filtration, and/or primary and secondary fluid contacting operations.

For example, the stacked plate assembly of FIG. 24 is arranged for mass transfer contacting of a primary fluid and a secondary fluid. The primary fluid is introduced in liquid inlet conduit 830, flowed across the flow channels of the constituent filter plates to a liquid outlet, and discharged from the system in liquid outlet conduit 836. The secondary fluid is introduced into the stacked assembly via secondary fluid inlet conduit 846, flowed through the filter element interior passages from the L-shaped channels of the paired plates in proximity to the secondary fluid inlet to the L-shaped channels diagonally opposite the first L-shaped channels, for discharge of secondary fluid from the stacked assembly in secondary fluid outlet conduit 840.

As an alternative to the stacked plate assembly shown in FIG. 24, the assembly may be constructed for normal filtration operation, with permeate being withdrawn from one set of L-shaped channels, in communication with the plate openings 850 and 840, via outlet conduit 841, and with permeate being withdrawn from the other set of L-shaped channels, in communication with plate openings 860 and 844, via conduit 846, so that permeate flows out of the conduit 846 opposite to the direction indicated by the arrow.

Alternatively, there may be provided corresponding openings in gasket 820 and mounting plate 800, communicating with openings 860 and 840 of the respective lower and upper filter plates, to withdraw permeate through a conduit joined to the mounting plate 800, analogous to withdrawal conduit 841.

The stacked filter array thus is built up by stacking plates in respective inverted facing pairs until a predetermined height of stacked plates is obtained, followed by placement over the stacked plate assembly of the top end plate 828. Each of the respective rods 802, 804, 806, and 808 is threaded on its upper outer surface for mating with complementarily threaded mechanical fasteners, such as the washer and nut assemblies shown, comprising washers 870 and nuts 872. Note that the triangular rod is threaded on its upper apex extremities, for such purpose.

While the invention has been described with reference to specific illustrative embodiments, it will be apparent that there are other variations, modifications, and embodiments possible within the broad scope of the invention, and that all such variations, modifications, and embodiments are to be regarded as being within the spirit and scope of the invention as hereinafter claimed.

What is claimed is:

1. A filter plate having a generally rectangular and generally planar shape with a substantially flat bottom surface, a top surface with a first upwardly extending wall circumscribingly bounding a flow channel of generally rectangular shape, and a second upwardly extending wall interior to and of lesser height than the first bounding wall, the second wall being in spaced relation to the first wall along diagonally opposed L-shaped peripheral sections of the flow channel, said first and second walls defining an L-shaped channel there between in said diagonally opposed L-shaped peripheral sections each L-shaped channel comprising a leg extending transversely across the flow channel for a major portion of the width thereof, and a leg extending longitudinally for a portion of length of the flow channel and each longitudinal leg communicating at is extremity with an opening extending through the plate, ridges extending between the first and second bounding walls along peripheral portions of the flow channel not comprising said L-shaped peripheral sections; a liquid inlet port at a first side of the flow channel and a liquid outlet port at a second side of the flow channel opposite the first side thereof, the liquid inlet port being joined in liquid flow communication with a liquid flow feed trough located interior of said second wall and extending transversely across the first side of the flow channel, and the liquid outlet port being joined in liquid flow communication with a liquid collection trough located interior of said second wall and extending transversely across the second side of the flow channel, with a plurality of spaced-apart partitions extending upwardly from the floor of the flow channel between the liquid feed trough and the liquid collection trough, the partitions being of substantially the same height as the second bounding wall and substantially parallel to one another to define a series of sub-channels between the partitions, extending longitudinally between the liquid feed trough and the liquid collection trough.

2. A filter plate according to claim 1, formed of a material of construction selected from the group consisting of polyethylene, polypropylene, polysulfone, polyvinylidene fluoride, polytetrafluoroethylene, ceramics, polyimides, glass, metal, polyvinyl chloride, regenerated cellulose, cellulose acetate, cellulose triacetate, cellulose nitrate, and mixtures, alloys, and composites thereof.

3. A stacked-plate filter, comprising:
 (a) a first filter plate having a generally rectangular and generally planar shape with a substantially flat bottom surface, a top surface with a first upwardly extending wall circumscribingly bounding a flow channel of generally rectangular shape, and a second upwardly extending wall interior to and of lesser height than the first bounding wall, the second wall being in spaced relation to the first wall along diagonally opposed L-shaped peripheral sections of the flow channel, said first and second walls defining an L-shaped channel therebetween in said diagonally opposed L-shaped peripheral sections, each L-shaped channel comprising a leg extending transversely across the flow channel for a major portion of the width thereof, and a leg extending longitudinally for a portion of length of the flow channel and each longitudinal leg communicating at its extremity with an opening extending through the plate, ridges extending between the first and second bounding walls along peripheral portions of the flow channel not comprising said L-shaped peripheral sections, a liquid inlet port at a first side of the flow channel and a liquid outlet port at a second side of the flow channel opposite the first side thereof, the liquid inlet port being joined in liquid flow communication with a liquid feed trough located interior of said second wall and extending transversely across the first side of the flow channel, and the liquid outlet port being joined in liquid flow communication with a liquid collection trough located interior of said second wall and extending transversely across the second side of the flow channel with a plurality of spaced-apart partitions extending upwardly from the flow of the flow channel between the liquid feed trough and the liquid collection trough, the partitions being of substantially the same height as the second bounding wall and substantially parallel to one another to define a series of sub-channels between the partitions, extending longitudinally between the liquid feed trough and the liquid collection trough;
 (b) a second filter plate of corresponding structure to said first filter plate and mated with said first filter plate in invertedly positioned facing relationship thereto, such that said first and second filter plates corporately form an enclosed flow channel;
 (c) a filter element positioned in said enclosed flow channel and constructed and arranged for passing filtrate into said L-shaped channels;
 (d) means for introducing solids-containing liquid to said liquid inlet port;
 (e) means for discharging solids-depleted liquid from said liquid outlet port; and
 (f) means for discharging filtrate from the opening in said L-shaped channels.

4. A filter plate according to claim 1, having mounting openings at each of its corners outside the first peripheral wall, wherein said openings comprise at least two different cross-sectional opening shapes.

5. A stacked plate assembly, comprising:
 (a) a first filter plate having a generally rectangular and generally planar shape with a substantially flat bottom surface, a top surface with a first upwardly extending wall circumscribingly bounding a flow channel of generally rectangular shape, and a second upwardly extending wall interior to and of lesser height than the first bounding wall, the second wall being in spaced relation to the first wall along diagonally opposed L-shaped peripheral sections of the flow channel, said first and second walls defining an L-shaped channel therebetween in said diagonally opposed L-shaped peripheral sections, each L-shaped peripheral section comprising a leg extending transversely across the flow channel for a major portion of the width thereof, and a leg extending longitudinally for a portion of the length of the flow channel and communicating at its extremity with an opening extending through the plate, ridges extending between the first and second bounding walls along peripheral portions of the flow channel not comprising said L-shaped peripheral sections; a liquid inlet port at a first side of the flow channel and a liquid outlet port at a second side of the flow channel opposite the first side thereof, the liquid inlet port being joined in liquid flow communication with a liquid feed trough located interior of said second wall and extending transversely across the first side of the flow channel, and the liquid outlet port being joined in liquid flow communication with a liquid collection trough located interior of said second wall and extending transversely across the second side of the flow channel, with a plurality of spaced-apart partitions extending upwardly from the floor of the flow channel between the liquid feed trough and the liquid collection trough, the partitions being of substantially the same height as the second bounding wall and substantially parallel to one another to define a series of sub-channels between the partitions extending longitudinally between the liquid feed trough and the liquid collection trough;
 (b) a second filter plate of corresponding structure to said first filter plate and mated with said first filter plate in invertedly positioned facing relationship thereto, such that said first and second filter plates corporately form an enclosed flow channel; and
 (c) a filter element positioned in said enclosed flow channel and constructed and arranged for passing filtrate into said L-shaped fluid flow channels.

6. A filter plate having a generally rectangular and generally planar shape with a substantially flat bottom surface, and a top surface having a first upwardly extending wall circumscribingly bounding a flow channel of generally rectangular shape, and a second upwardly extending wall interior to and of lesser height than the first bounding wall, the second wall being in spaced relation to the first wall along diagonally opposed L-shaped peripheral sections of the flow channel, said first and second walls defining an L-shaped channel therebetween in said diagonally opposed L-shaped peripheral sections, each L-shaped channel comprising a leg extending transversely across the flow channel for a major portion of the width thereof, and a leg extending longitudinally for a portion of the length of the flow channel and each longitudinal leg communicating at its extremity with an opening extending through the plate, a liquid inlet port at a first side of the flow channel and a liquid outlet port at a second side of the flow channel opposite the first side thereof, the liquid inlet port being joined in liquid flow communication with a liquid feed trough located interior of said second wall and extending transversely across the first side of the flow channel, and the liquid outlet port being joined in liquid flow communication with the liquid collection trough located interior of said second wall and extending transversely across the second side of the flow channel a plurality of spaced-apart partitions extending upwardly from the floor of the flow channel between the liquid feed trough and the liquid collection trough; the partitions being of substantially the same height as the second wall and substantially parallel to one another to define a series of sub-channels between the partitions, extending longitudinally between the feed trough and the liquid collection trough; wherein the liquid inlet port has an open area, designated $A_o$, and each sub-channel in said series of channels extending longitudinally between the feed trough and the collection trough, has an open area, designated $A_I$, measured in a plane perpendicular to the longitudinal axis of the longitudinally extending sub-channel, of a height equal to the height of the partitions bounding said longitudinally extending sub-channels and a width equal to the transverse distance between adjacent spaced-apart partitions bounding said longitudinally extending sub-channels, wherein $A_o$ is from about 0.8 to about 1.3 times the total longitudinally extending sub-channel open area $A_s$, wherein and n is the number of longitudinally extending channels.

UNITED STATES PATENT AND TRADEMARK OFFICE
CERTIFICATE OF CORRECTION

PATENT NO. : 4,882,050
DATED : November 21, 1989
INVENTOR(S) : Henry B. Kopf

It is certified that error appears in the above-identified patent and that said Letters Patent is hereby corrected as shown below:

Column 16, line 26, after sub-channels, insert -- $\sum_{i=1}^{n} A_i$ --.

Column 16, line 29, change "cross-s" to --cross-sectional--.
Column 16, line 29, after "cross-s" insert --areas--.
Column 16, line 30, after "sub-channels" insert -- $\sum_{i=1}^{n} A_i$ --.

Column 16, line 31, change "ben" to --been--.
Column 28, line 9, change "$A_I$," to --$A_i$--.
Column 28, line 17-18, after "wherein" insert -- $A_s = \sum_{i=1}^{n} A_i$ --.

Signed and Sealed this

Nineteenth Day of November, 1991

Attest:

HARRY F. MANBECK, JR.

Attesting Officer

Commissioner of Patents and Trademarks